(12) United States Patent
Moenning et al.

(10) Patent No.: US 7,243,649 B2
(45) Date of Patent: Jul. 17, 2007

(54) ANESTHESIA ADMINISTRATION MASK AND EYE SHIELD

(75) Inventors: John Moenning, Noblesville, IN (US); Dennis Irlbeck, Noblesville, IN (US)

(73) Assignee: King Systems Corporation, Noblesville, IN (US)

( * ) Notice: Subject to any disclaimer, the term of this patent is extended or adjusted under 35 U.S.C. 154(b) by 102 days.

(21) Appl. No.: 10/647,991

(22) Filed: Aug. 26, 2003

(65) Prior Publication Data

US 2004/0069306 A1    Apr. 15, 2004

Related U.S. Application Data

(60) Provisional application No. 60/405,960, filed on Aug. 26, 2002.

(51) Int. Cl.
*A61M 15/00* (2006.01)

(52) U.S. Cl. .................. 128/203.12; 128/207.18; 128/204.18; 128/206.29

(58) Field of Classification Search .................. 128/203.11–203.15, 203.17, 205.22, 206.11, 128/206.18, 206.21, 207.18, 206.23, 201.12, 128/207.12, 205.24, 201.28, 207.16, 207.17
See application file for complete search history.

(56) References Cited

U.S. PATENT DOCUMENTS

| | | | |
|---|---|---|---|
| 146,730 A | | 1/1874 | Vickers |
| 812,706 A | | 2/1906 | Warbasse |
| 2,383,649 A | | 8/1945 | Heidbrink |
| 2,462,005 A | * | 2/1949 | Schauweker ............ 128/207.11 |
| 2,664,084 A | | 12/1953 | Hammermann |
| 2,743,727 A | | 5/1956 | Griesinger |
| 2,792,000 A | | 5/1957 | Richardson |
| 2,843,122 A | * | 7/1958 | Hudson ................. 128/207.13 |
| 2,848,994 A | | 8/1958 | Aguado |
| 2,868,198 A | | 1/1959 | Brooke |
| 2,954,027 A | | 9/1960 | Marasco |
| 3,426,755 A | | 2/1969 | Clegg |
| 3,721,238 A | | 3/1973 | Wise et al. |
| 3,747,599 A | | 7/1973 | Malmin |

(Continued)

OTHER PUBLICATIONS

Accutron, Inc., State of the Art, Nitrous Oxide Systems, www.accutron-inc.com/scripts/scavenging.asp.

(Continued)

*Primary Examiner*—Justine R. Yu
*Assistant Examiner*—Shumaya Ali
(74) *Attorney, Agent, or Firm*—E. Victor Indiano; Indiano Vaughan LLP

(57) ABSTRACT

An anesthesia delivery device can be coupled to a ventilation system. The device includes an inspiratory gas line having a machine end and a patient end. The machine end can be fluidly coupled to the ventilation system, and the patient end can be received within the naris of the patient. A face mask having a dome portion can cover the patient's nose without covering the patient's mouth and defines an inside air space between the patient's nose and the dome portion, and an outside air space exterior of the dome portion. A vent allows gas to pass between the inside and outside air spaces. An exhaust port can be fluidly coupled to the exhaust gas output. The exhaust port and vent can cooperatively exert a negative pressure on the outside air space for preventing inspiratory gas from entering the outside air space.

33 Claims, 18 Drawing Sheets

U.S. PATENT DOCUMENTS

| | | |
|---|---|---|
| 3,964,489 A | 6/1976 | Kesselring |
| 4,015,598 A | 4/1977 | Brown |
| 4,032,970 A | 6/1977 | Anderson |
| D250,131 S | 10/1978 | Lewis et al. |
| 4,164,942 A | 8/1979 | Beard et al. |
| 4,192,307 A | 3/1980 | Baer |
| 4,193,407 A | 3/1980 | Edmark |
| 4,219,020 A | 8/1980 | Czajka |
| 4,231,363 A | 11/1980 | Grimes |
| 4,265,239 A | 5/1981 | Fischer, Jr. et al. |
| 4,312,339 A | 1/1982 | Thompson, Sr. |
| 4,337,767 A | 7/1982 | Yahata |
| 4,344,758 A | 8/1982 | Wielhouwer et al. |
| 4,355,637 A | 10/1982 | Dyer |
| 4,402,316 A | 9/1983 | Gadberry |
| 4,417,573 A | 11/1983 | De Vries |
| 4,454,800 A * | 6/1984 | Koepper et al. ............... 91/51 |
| 4,454,881 A | 6/1984 | Huber et al. |
| 4,467,799 A | 8/1984 | Steinberg |
| 4,493,339 A | 1/1985 | Porter, Jr. |
| 4,503,851 A | 3/1985 | Braunroth |
| 4,513,741 A | 4/1985 | Demi |
| 4,520,809 A | 6/1985 | de Greef et al. |
| 4,541,698 A | 9/1985 | Lerner |
| 4,545,378 A | 10/1985 | Chrones |
| 4,770,169 A | 9/1988 | Schmoegner et al. |
| 4,807,617 A | 2/1989 | Nesti |
| 4,821,715 A * | 4/1989 | Downing ............... 128/207.18 |
| 4,889,490 A | 12/1989 | Jenkinson |
| 4,896,666 A | 1/1990 | Hinkle |
| 4,987,894 A | 1/1991 | Kight |
| 5,018,519 A | 5/1991 | Brown |
| D321,570 S | 11/1991 | Blasdell et al. |
| 5,069,205 A | 12/1991 | Urso |
| 5,109,839 A | 5/1992 | Blasdell et al. |
| 5,159,938 A | 11/1992 | Laughlin |
| 5,185,005 A * | 2/1993 | Ballantyne ................ 604/174 |
| 5,188,101 A | 2/1993 | Tumolo |
| 5,220,699 A | 6/1993 | Farris |
| 5,243,708 A * | 9/1993 | Vanuch .......................... 2/206 |
| 5,243,971 A | 9/1993 | Sullivan et al. |
| 5,261,398 A * | 11/1993 | Sobolik ................ 128/206.23 |
| 5,311,862 A | 5/1994 | Blasdell et al. |
| D353,198 S | 12/1994 | Blasdell et al. |
| 5,400,781 A * | 3/1995 | Davenport ............. 128/206.28 |
| 5,404,873 A | 4/1995 | Leagre et al. |
| 5,419,317 A * | 5/1995 | Blasdell et al. ........ 128/205.19 |
| 5,474,060 A * | 12/1995 | Evans ................... 128/204.22 |
| 5,538,000 A * | 7/1996 | Rudolph ................ 128/205.25 |
| 5,538,013 A | 7/1996 | Brannon |
| 5,657,752 A | 8/1997 | Landis et al. |
| 5,687,715 A | 11/1997 | Landis et al. |
| 5,765,553 A | 6/1998 | Richards et al. |
| 5,813,423 A | 9/1998 | Kirchgeorg |
| 5,837,904 A | 11/1998 | Porter |
| 5,839,433 A | 11/1998 | Higenbottam |
| 5,887,587 A | 3/1999 | Groenke |
| 5,901,705 A | 5/1999 | Leagre |
| 5,937,852 A | 8/1999 | Butler et al. |
| 6,012,455 A * | 1/2000 | Goldstein .............. 128/207.18 |
| 6,016,801 A | 1/2000 | Philips |
| 6,044,844 A | 4/2000 | Kwok et al. |
| 6,079,980 A | 6/2000 | Durand |
| 6,085,748 A | 7/2000 | Sword et al. |
| 6,112,746 A | 9/2000 | Kwok et al. |
| 6,119,694 A | 9/2000 | Correa et al. |
| 6,135,109 A | 10/2000 | Blasdell et al. |
| 6,192,886 B1 | 2/2001 | Rudolph |
| 6,213,125 B1 | 4/2001 | Reese et al. |
| 6,216,695 B1 | 4/2001 | Ruben |
| 6,305,375 B1 | 10/2001 | Brown |
| 6,412,488 B1 * | 7/2002 | Barnett et al. ......... 128/207.13 |
| 6,439,231 B1 | 8/2002 | Fukunaga et al. |
| 6,494,206 B1 | 12/2002 | Bergamaschi et al. |
| 6,494,207 B1 | 12/2002 | Kwok |
| 6,523,179 B1 | 2/2003 | Zegarelli et al. |
| 6,532,598 B1 | 3/2003 | Cardarelli |
| 2003/0094178 A1 * | 5/2003 | McAuley et al. ...... 128/207.18 |

OTHER PUBLICATIONS

King Systems Corporation, "Selected Reprints of Web-site papers showing prior art face masks, scented masks and other products", Aug. 27, 2003.
Porter Instrument Company, Inc., Nitrous Oxide Scavenger System, www.porterinst.com/conscav.html.
MedQue.com CPR Microshield, Item No. 70150 (p. 1 of 1).
Ambu® Disposable Face Masks; Ambu 150 Certified Sep. 1996, (p. 1 of 1).
Infection Control; Tie on Face Masks, Infec_206.
Infection Control; Earloop Face Mask; infec_205.
Porter Instrument Company, Inc., brochure, Revised Sep. 2002.
Porter Nitrous Oxide Sedation Systems, brochure, 6 pages.
Why the Porter Double Mask System is the Only Smart Choice!, Porter Instrument Company, Inc.,.
Porter Scavenger Retrofit Kits, Porter Instrument Company, Inc.
Anesthesia and Pain Control; "Clinical evaluation of the efficacy of three nitrous oxide scavenging units during dental treatment", Fred Certosimo, DMD, MSEd, reprinted from General Dentistry, Sep.-Oct. 2002.

* cited by examiner

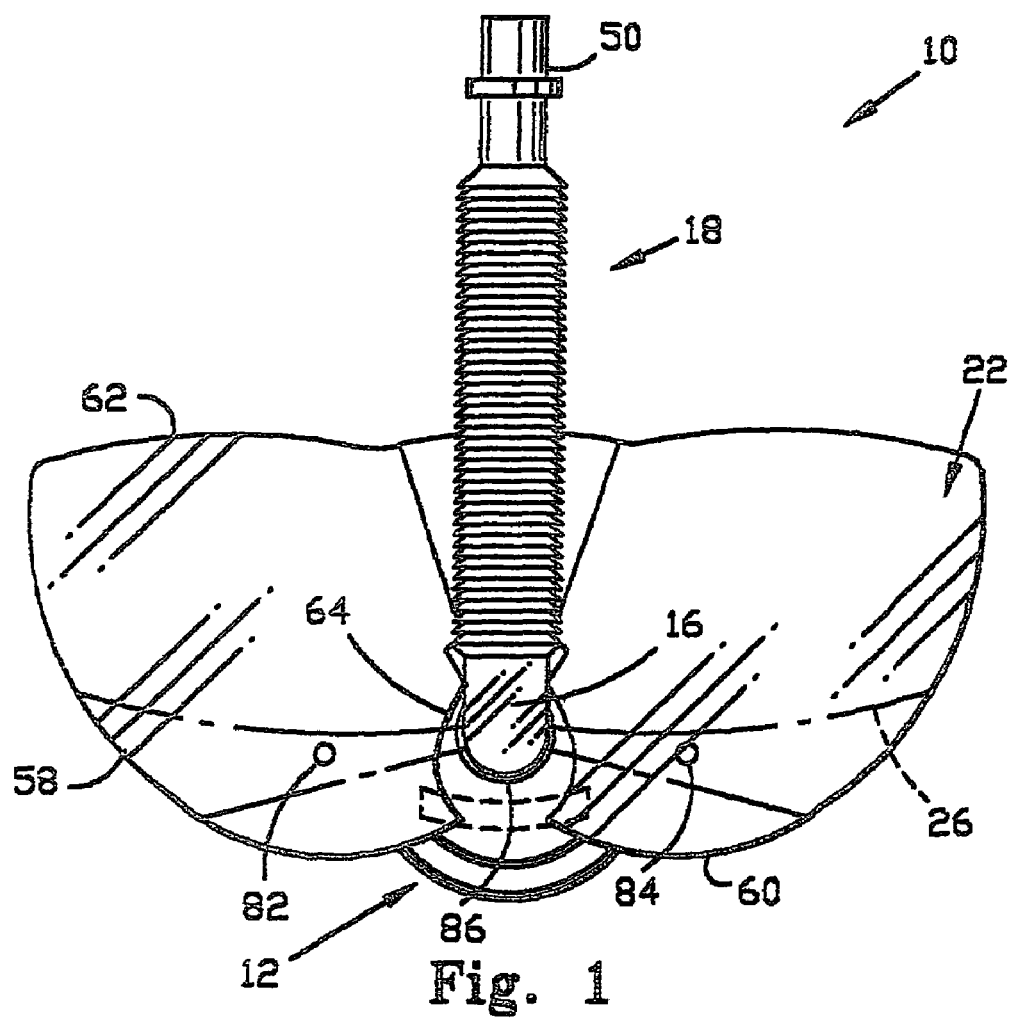

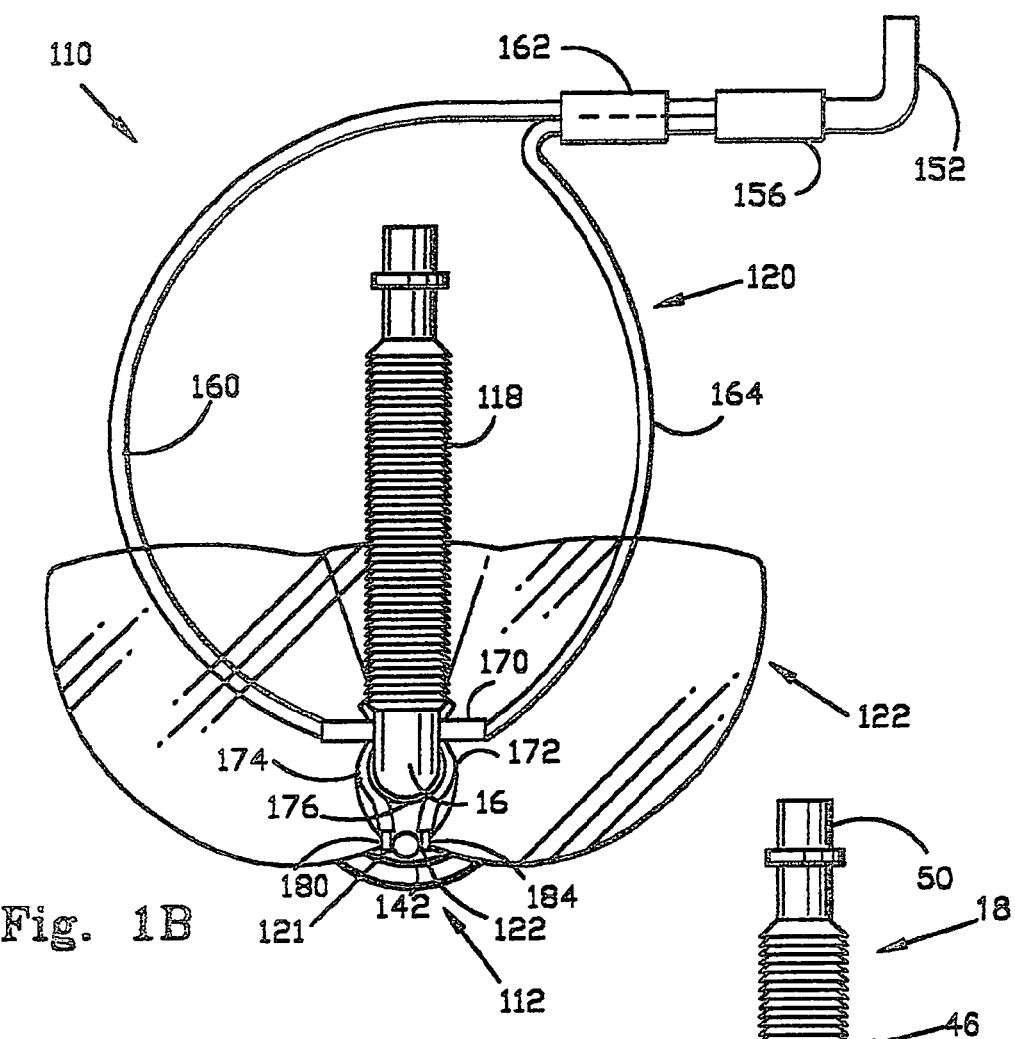
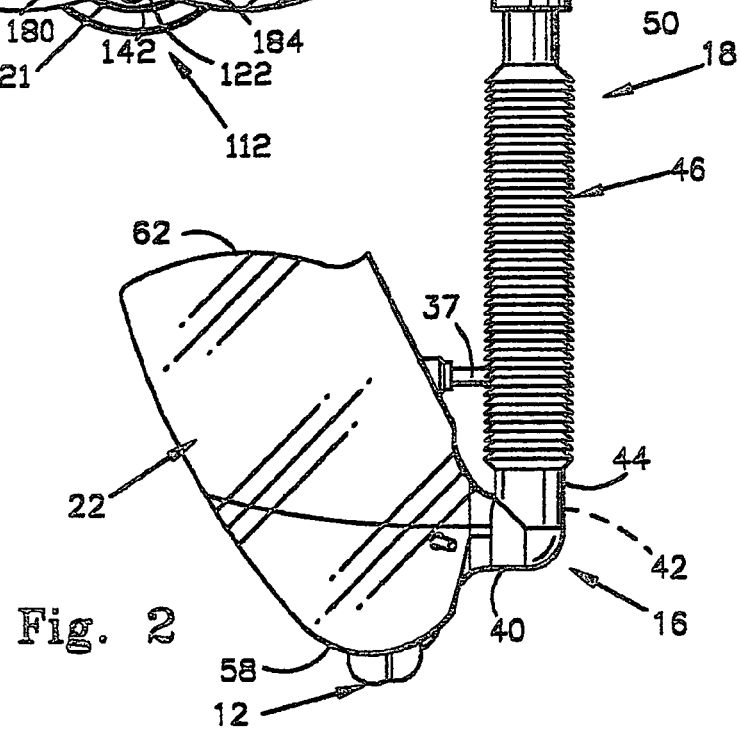

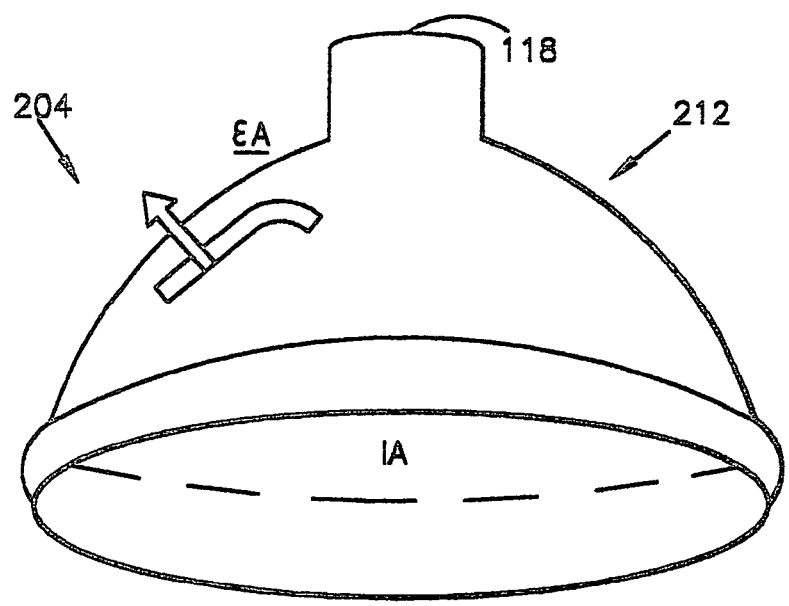
Fig. 8B
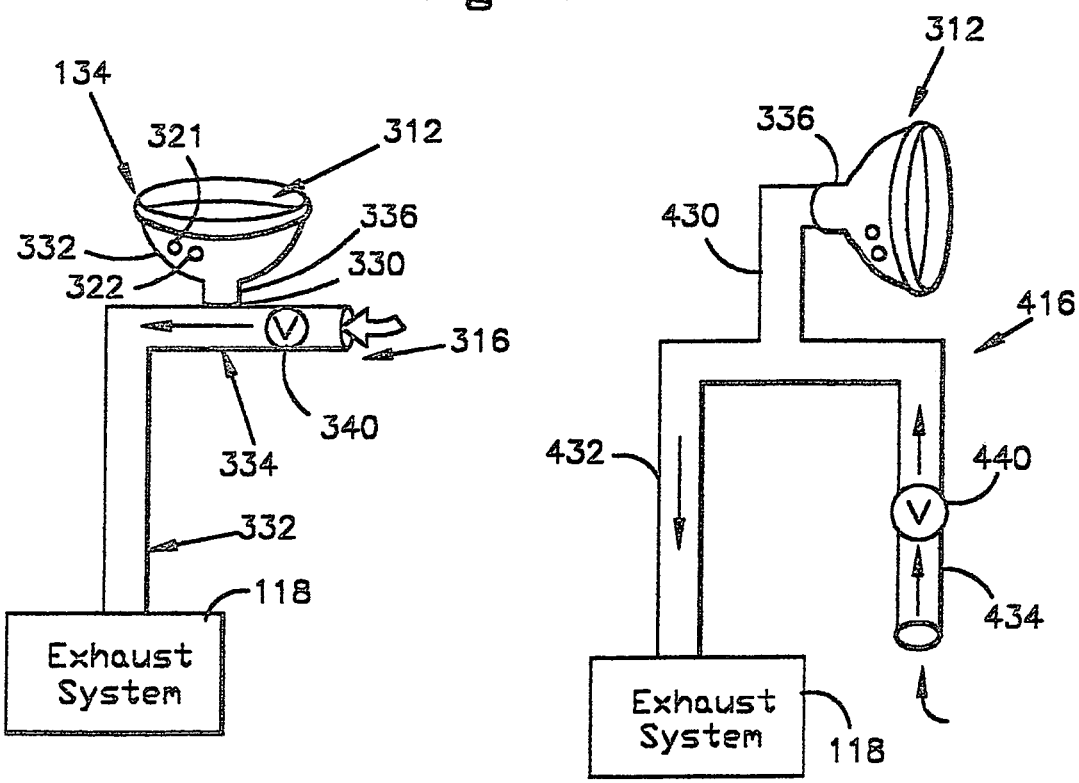
Fig. 9B
Fig. 10B

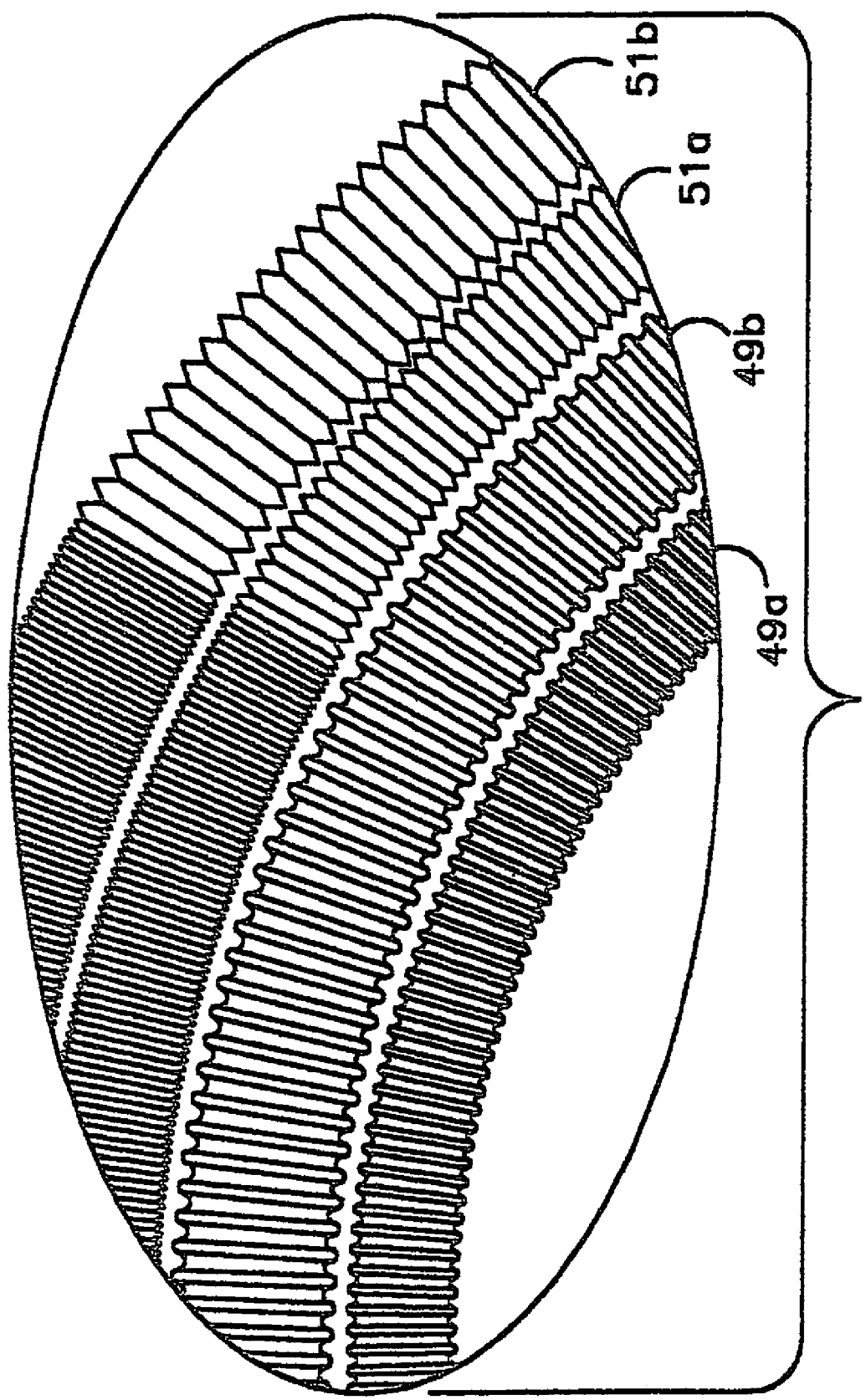

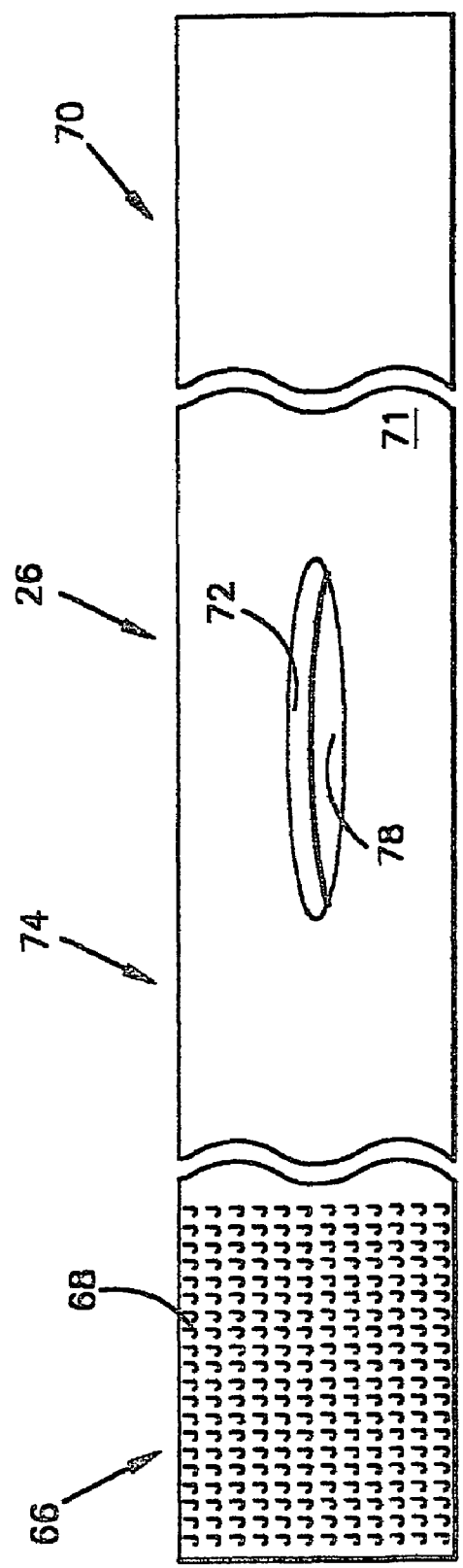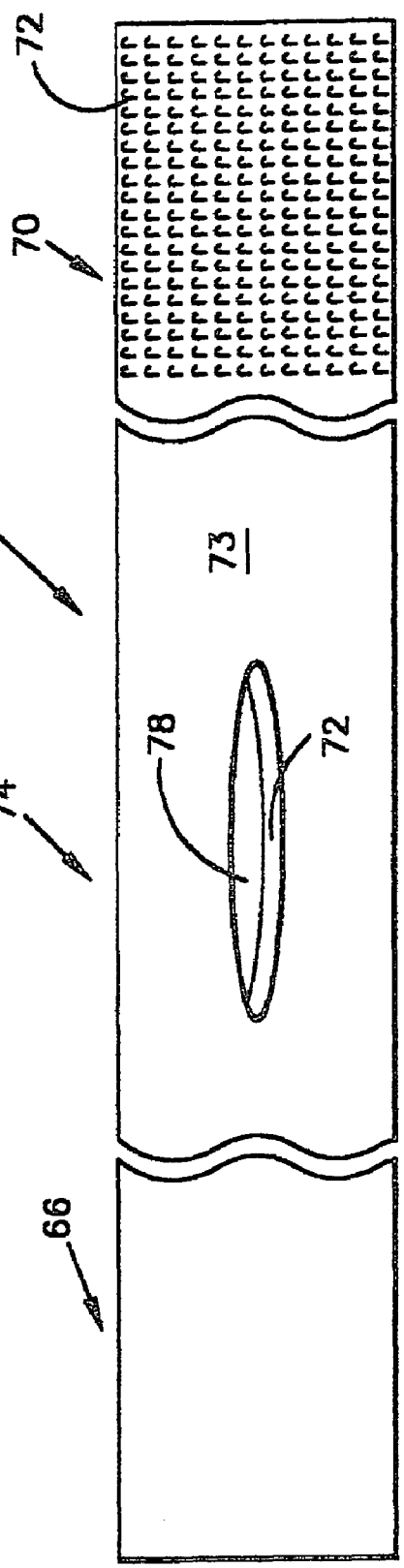

ANESTHESIA ADMINISTRATION MASK AND EYE SHIELD

STATEMENT OF PRIORITY

This application claims priority to Moenning, U.S. Provisional Application No. 60/405,960 filed Aug. 26 2002.

I. TECHNICAL FIELD OF THE INVENTION

The present invention relates to an anesthesia delivery device, and in particular, to an anesthesia delivery device that is particularly well-suited for use in the dental field, that includes a protective eye shield, and the ability to deliver inspiratory gases and scavenger expiratory gases.

II. BACKGROUND OF THE INVENTION

Certain dental procedures require the administration of anesthesia to a patient, in order to either block the pain that is incurred during the dental procedure, or to make the experience more pleasant for the patient. Often, this anesthetic takes the form of a local anesthesia such as lidocaine that is administered to the patient through a syringe and needle arrangement, and is injected at the site, such as the gum area, where the procedure is to be performed. In addition to this local anesthetic, many dental procedures also involve the administration of nitrous oxide to the patient. Unlike lidocaine, nitrous oxide is gaseous in form, and is administered to the patient before and during the course of the procedure, whereas lidocaine is administered prior to the procedure. Although nitrous oxide does not benefit the patient as significantly as the lidocaine from a "pain deadening" perspective, it does help to relax the patient. As such, nitrous oxide is administered as a general anesthetic to serve as a mild anesthetic and relaxant for the patient.

A large number of anesthetics are administered to patients in gaseous form, primarily within a non-dental surgical context. To administer these anesthetic gases to a patient, a face mask is used. Examples of such masks are the patient face masks manufactured by King Systems Corporation of Noblesville, Ind., that can be viewed at www.kingsystems.com. Although such anesthesia delivery masks, and in particular the masks manufactured by King, perform very admirably, and currently constitute the state-of-the-art standard in non-dental surgical anesthesia masks, dental procedures impose certain constraints upon the use of normal anesthesia face masks, that are not often found within a non-dental surgical arena.

One constraint relates to the area in which the dental procedure is performed. As most dental procedures are performed on the teeth and gums of the patient, the dentist performing the procedure must have access to the patient's mouth. Unfortunately, most surgical anesthesia masks are sized and configured to cover both the nose and mouth of the patient. As such, the use of a typically sized anesthesia mask on a dental patient prevents the dentist from obtaining access to the patient's mouth, unless the mask is removed.

Another constraint imposed by dental procedures is the requirement that the anesthesia mask be affixed to the patient for substantially the entire procedure, during which procedure the patient is usually kept awake. This requires that the dentist have some means for maintaining the mask in its proper position on the patient's face, and that the mask be secured in this position. Typically, in a non-dental surgical situation, this problem is not encountered, because an anesthesiologist is usually present. The anesthesiologist is not the person performing the surgical procedure on the patient, thus, the anesthesiologist can concentrate on placing and adjusting the mask on the patient's face in a proper position during the surgery without the responsibility of actually performing the surgery. Additionally, as the patient is usually fully "anaesthetized" during non-dental surgery, the patient is not inclined to move around during the surgery, making it easier to keep the mask in a fixed position.

Typically, during a non-dental surgical procedure, the anesthesiologist will hold the mask over the patient's nose and mouth for a sufficient time for the anesthesia to take effect. After the anesthesia has taken effect, the mask is removed from the anesthesia gas feed line, and replaced with an intubation tube, that extends down the patient's windpipe. The intubation tube may be securely attached to the patient by taping it to his face. This option is not available in most dental procedures, as the patient is not fully anaesthetized, thus making intubation an impractical alternative. As such, there is a need, during dental procedures, to employ some device for securing the mask in its proper position on the patient's face in a manner that frees the dentist's hands to perform the procedure.

Another constraint imposed by dental procedures is the requirement that the anesthesia mask be somewhat comfortable when affixed to the patient. Comfort is important because the mask is attached to the patient for substantially the entire procedure and the patient is usually kept awake during the procedure. In a non-dental procedure in which the patient is unconscious or the mask is not used for the entire procedure, it is not as important that the mask be comfortable on the patient, especially for any extended period of time.

Another complication in dental procedures relates to patient safety. Since the dental procedure often involves cutting, suturing and drilling, it is not unusual that human body fluids, (i.e. blood and saliva) and non-fluid items such as suture needles, tissue fragments, and dental materials will either become airborne or will be moving in close proximity to the eyes of the patient. In order to protect the patient's eyes, dentists heretofore have employed protective glasses to protect the eyes of patients. However, room for improvement exists in providing such eye protection, since these are difficult to wear and produce gas leaks with the current mask systems.

Because of these complications involving the administration of dental anesthetics, special masks that are adapted to dental procedures have been designed, and are in use. However, room for improvement exists regarding these known products. One area in which there exists a need for improvement relates to the containment of nitrous oxide within the dental surgical theater.

According to the American Dental Association, nitrous oxide, mixed with oxygen can be used in dental practices as a safe and effective method of managing pain and anxiety during dental procedures. Nitrous oxide usage benefits both the patient and the dental team members by providing a more comfortable visit with reduced patient stress. Using nitrous oxide sedation has few disadvantages to the patient. For the patient, the most significant potential hazard is hypoxia, although training in the administration of nitrous oxide can reduce the potential for this condition.

However, recent studies suggest that there exists the potential for hazards, due not to any one time exposure to nitrous oxide, but rather to frequent exposures to the gas on a long term basis. In particular, some studies suggest that women of child-bearing years, who are, or may become pregnant, may be affected adversely by long-term, frequent exposures to nitrous oxide.

In 1994, an article in the American Dental Association Journal discussed the use of nitrous oxide in dental practices. The ADA guidelines recommend nitrous oxide concentrations be maintained at or below 50 ppm. The committee that reviewed the nitrous oxide usage made five recommendations to the American Dental Association. One recommendation was that a better scavenger system be developed, to scavenge nitrous oxide that is administered to the patient, to better prevent the nitrous oxide from becoming resident within the dental surgical theater, where it could affect the dentist, hygienist, and other dental staff within the theater. A second suggestion was that a better nitrous oxide delivery system be designed.

The Applicant believes that the delivery and scavenger systems are extremely important in utilizing nitrous oxide. An important reason that these delivery and scavenger systems are important is that the primary persons at risk from, long-term, frequent exposure to nitrous oxide are women of child-bearing age. Such persons are frequently performing dental procedures, as the majority of dental assistants are female, and are between the age of 18 and 38 and a large number of dentists are female. These females, who are most likely to be exposed to frequent, long-term intervals of nitrous oxide, are the very people who are at greatest risk of being affected adversely by nitrous oxide. In this regard, some studies suggested that there exists an increased risk for spontaneous abortion with increased exposure to nitrous oxide. This increased risk leads many dentists to decline to use nitrous oxide in their practice.

Another concern relating to dental procedures relates to the use of eye protection. Although safety glasses are used throughout dentistry, the use of safety glasses or eye protection is becoming more wide-spread in other medical and dental specialties. This need for eye protection is highlighted by a case wherein a malpractice suit was brought against an orthodontist. It involved a wire injuring a patient. The particular wire was allegedly being bent by the orthodontist, popped out of his hands, and flew over multiple chairs, to land in a patient's eye, allegedly damaging the patient's eye. To avoid such injuries occurring to patients, and to reduce the risk of malpractice, many dentists, orthodontists and others have made the use of safety glasses routine procedure within their practice. Unfortunately, the use of safety glasses induces difficulties with nitrous oxide mask delivery and leakage.

Another concern relates to the comfort of the mask for the patient. Since the anesthesia mask is attached to the patient for substantially the entire procedure and the patient is usually kept awake during the procedure, it is preferable that the mask be somewhat comfortable when affixed to the patient. Several of the currently used dental masks are somewhat heavy and rigid, and are opaque. They also can have a plastic or rubber smell which can be unpleasant for the patient. These factors can induce a restricted, claustrophobic and otherwise uncomfortable feeling for the patient.

Due to these concerns expressed above, the Applicant sought to provide an improved dental mask that better isolates the nitrous oxide being delivered to the patient from the dental assistants and dentists performing a procedure. Additionally, in the preferred embodiment of the present invention, it is also an object of the present invention to provide an eye protection mechanism to increase patient safety; that can be securely coupled to a patient's head during the dental procedure in a manner that retains the mask in its desired position throughout the dental procedure and that is more comfortable for the patient.

III. SUMMARY OF THE INVENTION

In accordance with the present invention an anesthesia delivery device is disclosed for use on a patient having a mouth and a nose having a naris. The delivery device is capable of being coupled to a ventilation system having an inspiratory gas input for delivering gas to the patient and an exhaust gas output for delivering gas from a patient to the ventilation system. The anesthesia device comprises an inspiratory gas line having a machine end and a patient end. The machine end is capable of being fluidly coupled to the inspiratory gas input of the ventilation system, and the patient end is configured for being received within the naris of the patient for delivering inspiratory gas to the naris of the patient. The device also includes a face mask comprising a dome portion sized to cover the patient's nose without covering the patient's mouth. The dome portion defining an inside air space between the patient's nose and the dome portion, and an outside air space exterior of the dome portion. A vent is provided for allowing gas to pass between the inside air space and the outside air space. An exhaust port is provided that is capable of being fluidly coupled to the exhaust gas output of the ventilation system for allowing gas to pass from the inside air space to the exhaust gas output of the ventilation system. The exhaust port and vent are capable of cooperatively exerting a negative pressure on the outside air space adjacent to the face mask for preventing inspiratory gas from entering the outside air space adjacent to the face mask, and pulling in gases adjacent to the face mask.

Another feature of the present invention is that it includes an eye shield that covers the patient's face, thus helping to protect the patient against either bodily fluids or other objects from striking the patient's eye.

One feature of the present invention is that an inspiratory line system is provided that positions the ends of the lines in the nares of the patient. This features has the advantage of maximizing the delivery of anesthesia gas to the patient's respiratory tract, while minimizing the amount of gas lost through either leakage out of the mask to the exterior atmosphere, and to the vacuum driven exhaust gas scavenging system.

It is also a feature of the present invention that a vent is provided that permits air to flow from the area adjacent to the exterior of the mask to the interior of the mask. This feature has the advantage of allowing air to flow to the interior area of the mask, thus preventing the vacuum driven exhaust system from sucking air from the patient, which could lead to hypoxia. This feature also allows gases released through the patient's mouth to be scavenged by the exhaust system. Surprisingly, the presence of an appropriately designed vent permits this air flow without allowing any significant leakage of anesthesia gasses to the atmosphere exterior of the mask where it can contact the personnel in the dental procedure theater.

These and other features of the present invention will become more apparent to those skilled in the art in connection with a review of the drawings and detailed description of the invention set forth below.

V. BRIEF DESCRIPTION OF THE DRAWINGS

FIG. 1 is a front view of the dental mask and eye shield of the present invention;

FIG. 2 is a right side view of the present invention;

FIG. 13 is a side view of a variety of gas lines useable with the present invention;

FIG. 14 is a top view of the alternate embodiment strap shown in FIG. 10;

FIG. 15 is a bottom view of the alternate embodiment strap shown in FIG. 10;

FIG. 1B is a front view of a first alternate embodiment mask of the present invention;

FIG. 8B is a schematic plan view of a mask containing an alternate embodiment integral one-way flow valve;

FIG. 9B is a schematic view of an anesthesia device showing another alternate embodiment one-way flow valve; and FIG. 10B is a schematic view of an anesthesia device showing another alternate embodiment one-way flow valve.

VI DETAILED DESCRIPTION

A. First Embodiment of the Anesthesia Device of the Present Invention

Figure 8:
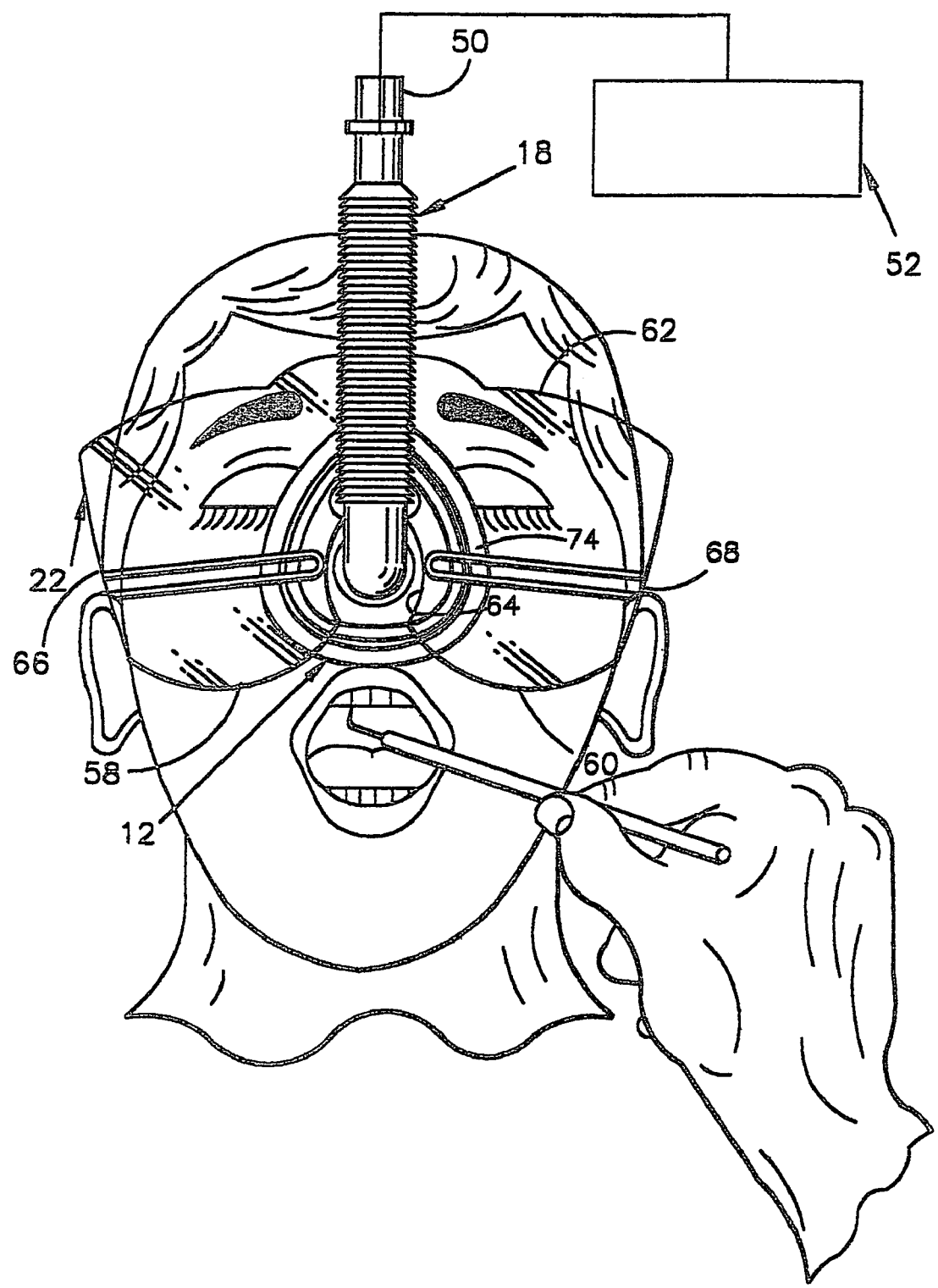
FIG. 8 is a front view of the present invention shown as being secured to a patient.

FIGS. 1-9 shows a first embodiment of a dental anesthesia device that includes a mask having an integrated eye protector 10 that includes an anesthesia mask 12, an elbow tube 16, a gas line 18, an eye mask 22, and a strap 26. The elbow tube 16 is coupled to an air tube fitting port 36 of the anesthesia mask 12. The gas line 18 is coupled at one end to the elbow tube 16 and, during use, is coupled at its other end to a gas outlet line of an anesthesia machine 52 (FIG. 8). The eye mask 22, shown as a sheet-like component, is coupled to the device 10 to provide eye protection for the patient. The strap 26 is coupled to the device 10 to hold the device 10 securely to the head of a patient during a procedure. FIG. 8 depicts the use of an endless elastic band type strap 68 that is coupled to the mask 12 by coupling the strap 68 to posts that extend outwardly from the front of the mask. First alternate embodiment strap 26 (which is the preferred strap) is probably best understood with reference to FIGS. 15 and 16. The anesthesia mask 12 is preferably an anesthesia mask similar to those currently manufactured by King Systems Corporation, and that can be viewed at King Systems' website at www.kingsystems.com. Unlike normal anesthesia face masks used in connection with a patient, the anesthesia face mask used in connection with the present invention is preferably a size 1 (neo-natal) or a size 2 (small pediatric) face mask. For normal, surgical procedures, size 1 and size 2 face masks are sized to cover the nose and mouth of neonatal or very young pediatric patients. However, the use of a neonatal or small pediatric sized face mask on an adult or older child patient only covers the nose of the patient. This ability of the anesthesia mask 12 to cover only the nose of the patient is valuable in a dental setting, since it leaves the mouth unobstructed, thus permitting the dentist to perform his procedure on the gums, teeth and/or mouth cavity of the patient. The anesthesia mask 12 can also be scented with a pleasant scent to reduce the stress of the patient while the mask is in use, and to make the experience generally more pleasant for the patient. Among the scenting materials that can be used to impart this pleasant scent, are scenting materials chosen from a group of scenting materials including fruit scented scenting materials, candy scented scenting materials, flower scented scenting materials, spice scented scenting materials, pottourri scented scenting materials, perfume scented scenting material, gum scented scenting materials, food scented scenting material, and plant scented scenting materials.

As best shown in FIGS. 3, 6, 7, 8, and 11, the anesthesia face mask 12 includes a tear-drop shaped frusto-conical crown member 32 having a lower edge to which is attached a lower circumferential cushion 34 to form a gas containment dome over the patient's nose. The lower circumferential cushion 34 generally comprises a hollow, tube-like bladder that preferably has a grooved surface 35 to help engage the circumferential cushion 34 with the skin of the patient it is pressed against. The hollow tube-like bladder of the lower circumferential cushion 34 can be filled with a gas, such as air. The bladder of the lower circumferential cushion 34 contains a supply of gas, so that it appears to be fully "inflated". Nonetheless, the gas pressure within the bladder is sufficiently low so as to allow the bladder to be easily conformed to the shape of the patient's face and to fit comfortably. To help the practitioner achieve the desired pressure, an air inflation valve 37 is provided that enables the practitioner to vary the air pressure within the bladder of the lower circumferential cushion 34. The frusto-conical crown member 32 includes a generally cylindrical air tube fitting port 36 that is formed at, and extends outwardly from the peak of the crown member 32. The frusto-conical crown member 32 also includes a right tab 82 and a left tab 84 located on the rights and left sides of the air tube fitting port 36 to position the eye shield 22.

As best shown in FIGS. 1 and 8, tabs 82, 84 can also serve as posts to which a strap 88 is anchored. The air tube fitting 36 has a diameter that is designed and sized to accept standard fittings of the type normally used for connection with an anesthesia mask. An elbow tube 16 (see FIGS. 5 and 6) is insertable into the air tube fitting port 36. The elbow tube 16 includes a patient end 40 that is designed and sized to interiorly receive the air tube fitting port 36 of the anesthesia mask 12; and a machine end 42 that is designed to be matingly integrally received by a patient end 44 of a gas transport tube 18.

Figure 11:
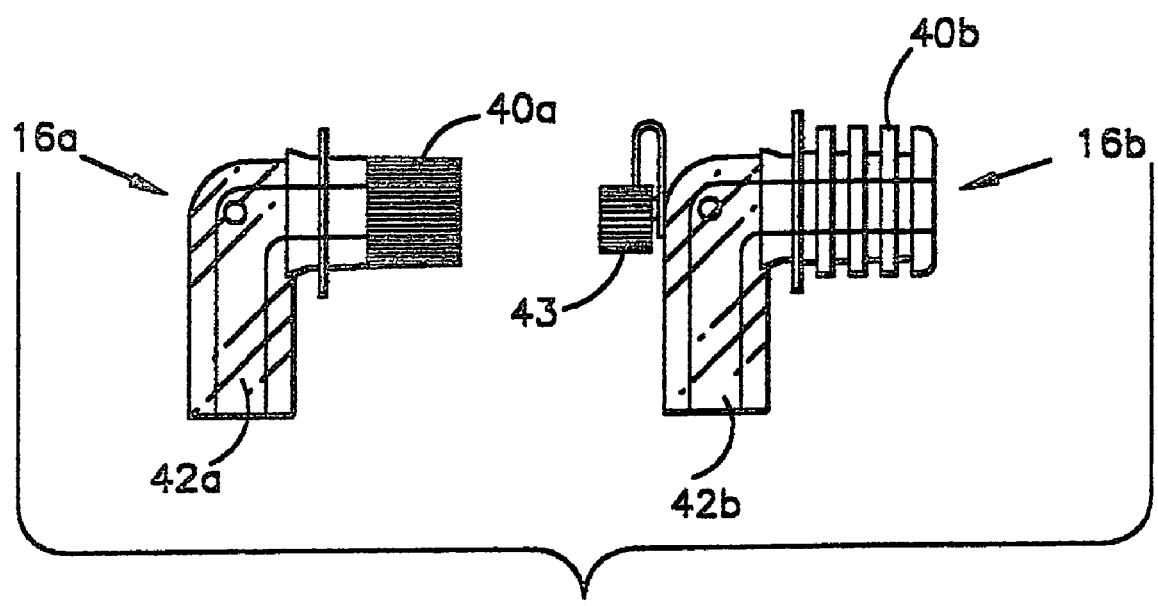
FIG. 11 is a side view of a pair of elbow connectors useable with the present invention.
Figure 12:
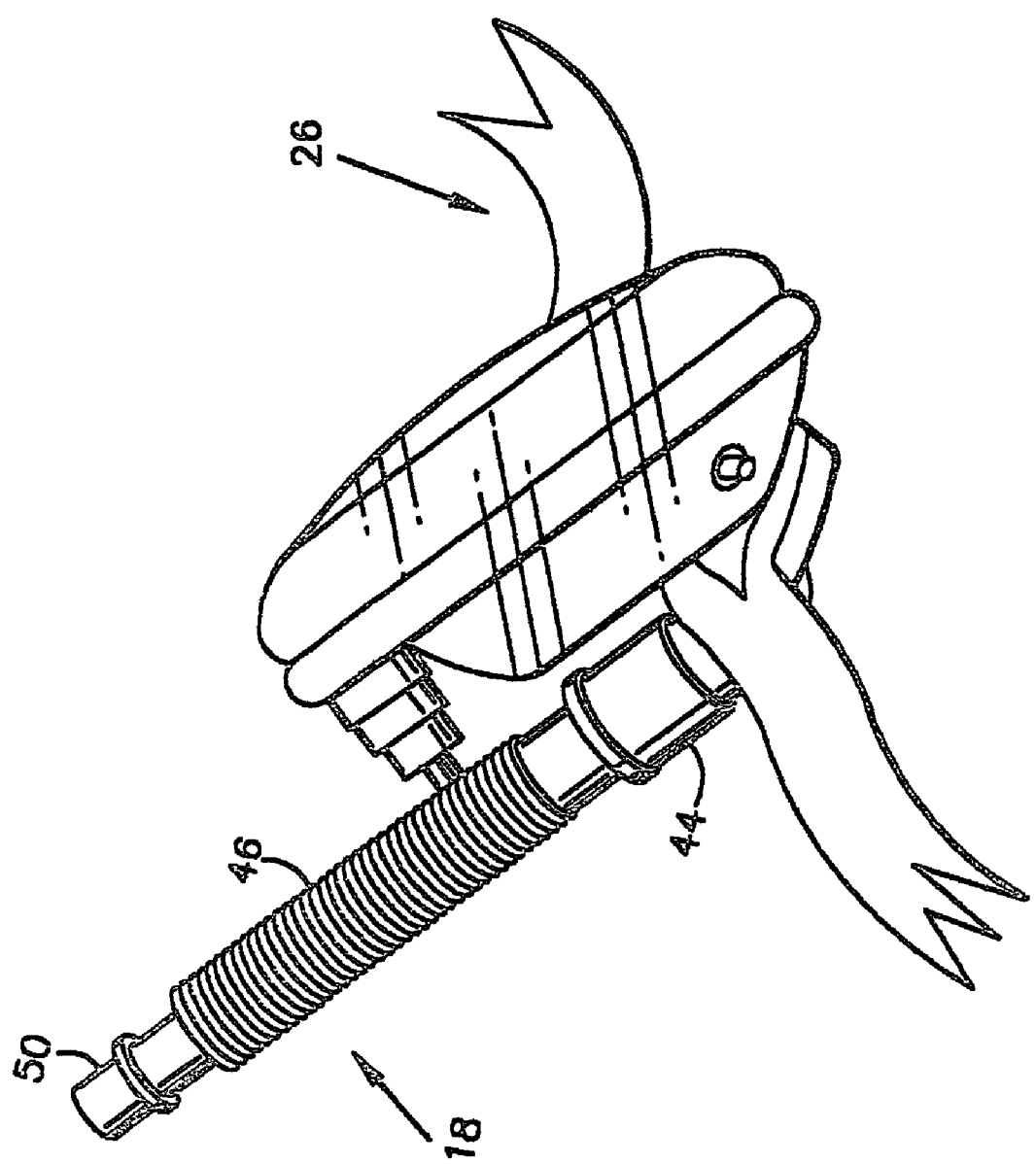
FIG. 12 is a left side view of the present invention with the alternate embodiment strap of FIG. 10.

FIG. 11 shows a pair of elbow tubes 16a, 16b that can be used in connection with the present invention. Elbow tube 16a is a standard elbow tube, having a patient end 40a and a machine end 42a. Similarly, second elbow tube 16b is generally similar to the first elbow tube 16a, except the second elbow tube 16b includes a sampling port 43 that has a sampling port cap 45. The cap 45 permits the sampling port 43 to be either opened or closed. The sampling port 43 is preferably threaded with a bayonet-type mount to engage a fitting, if necessary. The function served by the sampling port 43 is to permit the user to insert either a gas line, or a sampling device into the port. For example, the user might desire to insert a carbon dioxide ($CO_2$) and/or oxygen sampling device into the sampling port 43, to determine the oxygen and/or $CO_2$ content of the air in the face mask 12, to thereby monitor the patient's condition, including to help ensure that the patient does not become hypoxic.

Figure 9:
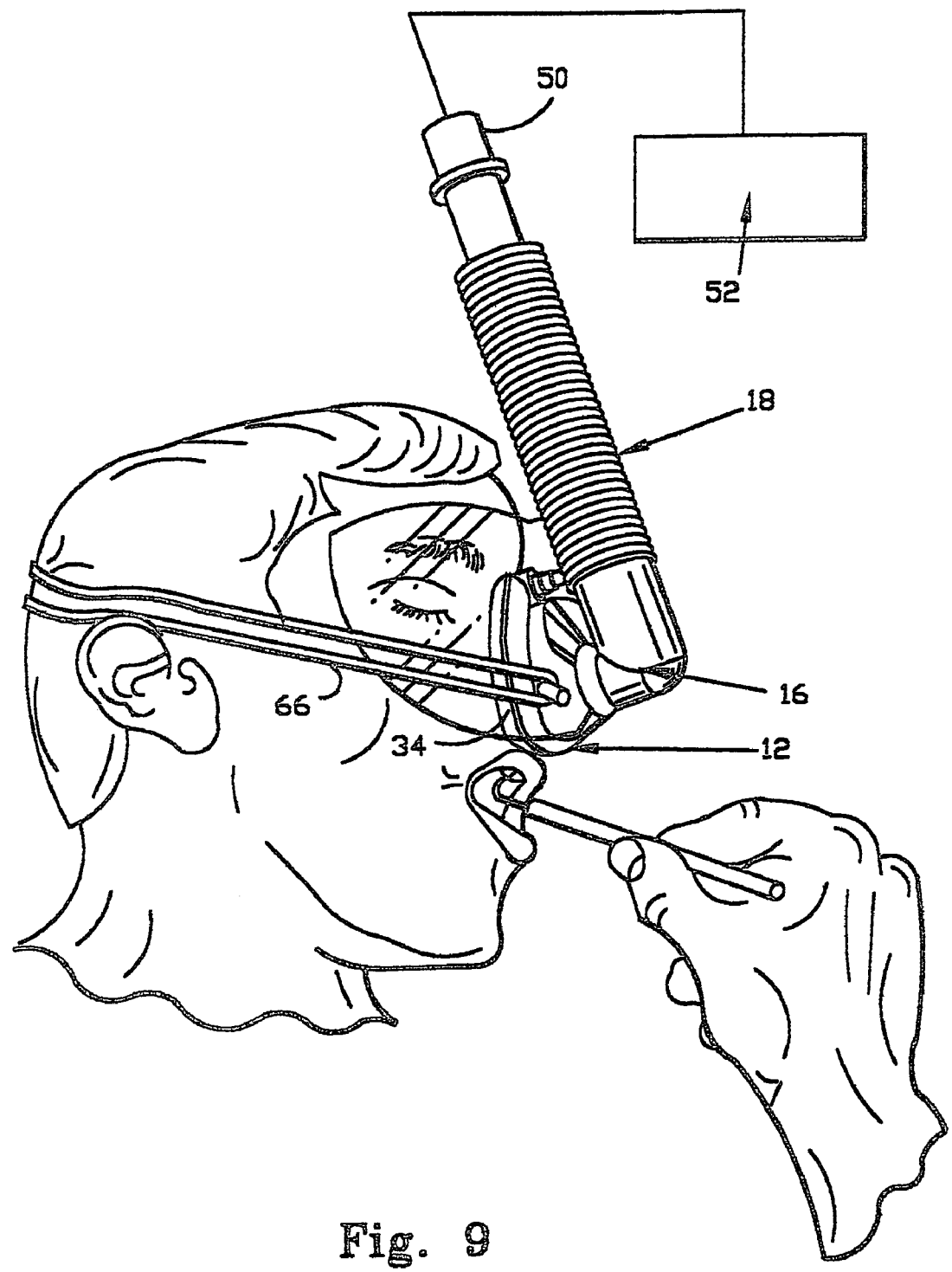
FIG. 9 is a left perspective view of the present invention, showing the device secured to a patient.

The gas line 18 comprises a segment of tubing having a patient end 44 that is coupled to the elbow tube 16, and a machine end 50 that can be coupled to an anesthesia delivery machine 52 (FIGS. 8 and 9). The gas delivery tube 18 is preferably of a standard size and shape to matingly connect both to the elbow tube 16 and the anesthesia machine 52.

In one embodiment, the gas tube 18 is a single-lumen non-rebreathing circuit type tube. Since the patient's mouth will be open, the patient will be able to inhale a mixture of anesthetic gas and air that is transported to the patient's nose through the gas tube 18 into the face mask 12, and exhale wasted carbon monoxide and gas through the patient's mouth. Alternately, a duel-lumen rebreathing circuit, that includes separate lumens for inhalation gas and exhalation gas may be used for gas tube 18. Examples of such dual-lumen rebreathing circuits are is the KING SYSTEMS CORPORATION F-1 Circuit, and the KING SYSTEMS CORPORATION F-2 Circuit, both of which can be viewed at the King Systems Corporation website at www.kingsystems.com, and that are also the subject of patents granted to Michael Leagre and Kevin Burrow; and other patents granted to Atsuo Fukunaga and Blanca Fukunaga.

Turning now to FIG. 14, two types of acceptable single-lumen tubing for the gas line 18 are shown, each of which comes in two different sizes. The first type of tubing shown is normal, corrugated tubing, such as 15 mm diameter tubing 49a and 22 mm diameter tubing 49b. The second type of tubing shown is ULTRA-FLEX® brand tubing which is also available in 15 mm diameter 51a and 22 mm diameter 51b sizes.

The corrugated tubing 49a, 49b is corrugated to help prevent kinking. The corrugated tubing can also be expanded or contracted in length. However, even though expandable, the corrugated tubing such as tubing 49a, 49b, usually has a fixed rest length. As such, if the tubing is pulled or stretched, pressure will be exerted on the tubing to shrink the tubing length back to its rest length.

Conversely, the ULTRA-FLEX® tubing is designed to have a variable, fixable length. The ULTRA-FLEX® tubing type samples 51a, 51b are designed to have an accordion-type corrugation structure. The user can shorten the effective rest length of the ULTRA-FLEX® tubing by compressing the accordion members together, such as is shown in the upper portion of both tubes 51a, 51b, or lengthen the effective rest length of the ULTRA-FLEX® tubing by expanding or pulling apart the accordion members, such as is shown in the lower portions of the flex tube members 51a, 51b. The ULTRA-FLEX® tubing differs from the corrugated tubing, in that if the user increases the length of the ULTRA-FLEX® tubing, such as by stretching the accordion members, the release of extension-biased pressure on the ULTRA-FLEX® tubing does not cause the ULTRA-FLEX® tubing to shrink back to its original rest length, but rather, it assumes the rest length to which it was stretched. Similarly, a shortening of the length of the ULTRA-FLEX® tubing by compressing the accordion style corrugations together will result in the ULTRA-FLEX® tubing 51a, 51b acquiring a new shortened rest length.

The eye shield member 22 shown in FIGS. 1, 2, 5, 6 and 7 of the drawings comprises a generally thin, sheet like member that is preferably made from a transparent, clear or tinted sheet of material. If desired, the sheet can be heat stamped or formed to have a three-dimensional curvature. Alternately, the sheet can be thin, flexible and generally planar. The eye piece member 22 includes a right lower lobe portion 58 that rests against the patient's cheekbone below her right eye; and a left lower lobe portion 60 that rests against the patient's cheekbone below her left eye. An upper curvilinear, three segment edge 62 is formed at the top of the eye piece 22 to rest against the patient's forehead, adjacent to her eyebrows, as best shown in FIGS. 8 and 9.

The eye mask 22 can be designed to be relatively inexpensive, as its primary purpose is to shield the patient's eyes from fluid, tissue and equipment debris within the surgical theater. Since the patient is not performing any intricate procedure while gazing through the eye mask 22, the eye mask 22 need not be designed to be optically correct, or perfectly clear, thus reducing the cost of producing the eye sheet 22, when compared to sunglass-type glasses.

The eye mask 22 also includes a generally elongated central cut-out portion 64 that is centrally disposed along the lower edge of the eye piece 22, an upper aperture 80 located above the central cut-out portion 64, and a right-side aperture 83 and a left-side aperture 85 located on the right and left sides of the central cut-out portion 64. The central cut out portion 64 is sized, shaped and positioned for receiving the elbow tube 16. The upper aperture 80 is sized, shaped and positioned for receiving the air inflation valve 37. The right-side aperture 83 is sized, shaped and positioned for receiving the right-side tab 82; and the left-side aperture 85 is sized, shaped and positioned for receiving the left-side tab 84, for securing the eye piece 22 onto the elbow 16 and mask 12, to thereby secure the eye piece 22 onto the device 10. In addition a double-sided segment of tape 86 is positioned on the outside of the crown member 32 of the anesthesia mask 12 below the air tube fitting port 36 to attach the lower part of the central cut-out portion 64 of the eye shield 22 to the anesthesia mask 12.

Figure 10:
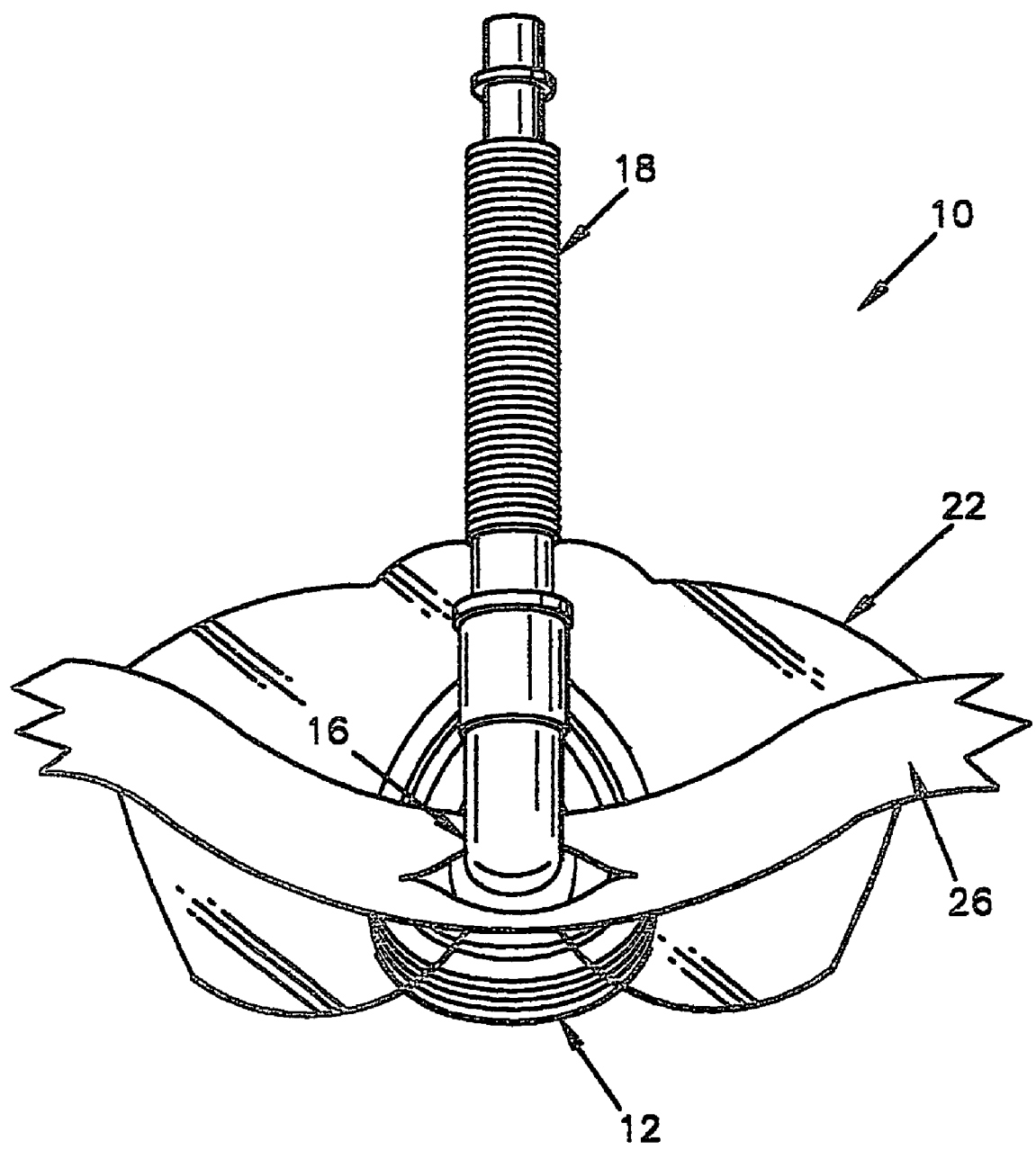
FIG. 10 is a front side view of the present invention illustrating an alternate embodiment strap.
Figure 16:
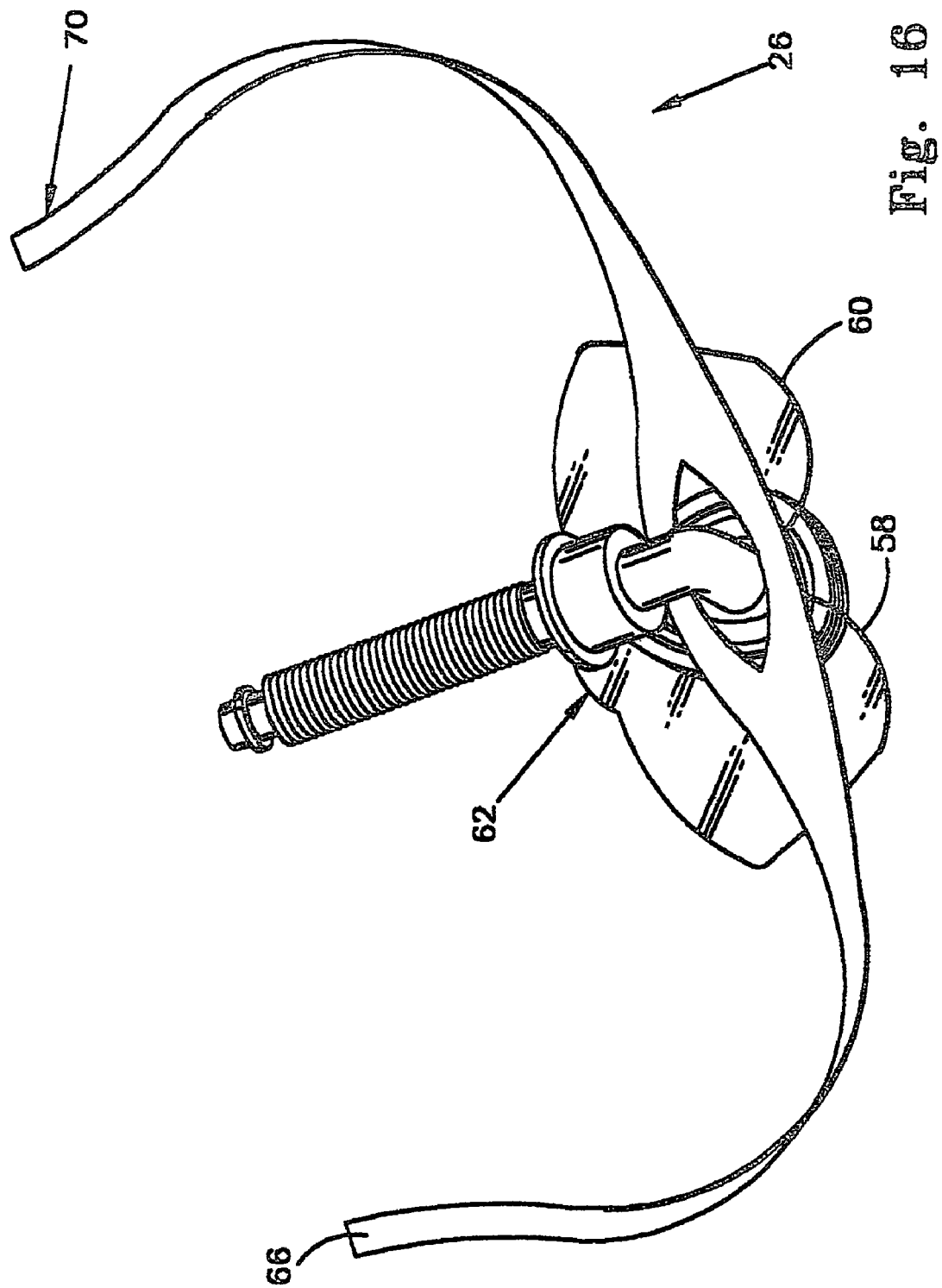
FIG. 16 is a top perspective view of the mask of the present invention containing the alternate embodiment strap of FIG. 10.

The strap 26 that is used for securing the device 10 onto the head of the patient is best shown with reference to FIGS. 10, 14 and 16. The strap 26 includes a first end 66, a second end 70, and a middle portion 74 disposed between the ends 66, 70. The strap 26 includes two major generally planar surfaces: an upper surface 71 and a lower surface 73. A slit like opening 72 extends longitudinally and is disposed generally in the middle portion 74 of the strap 26 to define a slitted aperture 78. The aperture 78, as shown in FIG. 16, is sized and configured for receiving the elbow tube 16, for securing the strap 26 onto the elbow 16, and thereby securing the strap 26 onto the device 10.

A fastener system is used to enable the user to fasten the first end 66 of the strap 26 to the second end 70 of the strap 26, to secure the strap 26 to the patient's head. Typically, the length of the strap 26 is long enough so that the first and second ends 66, 70 may be joined at the back of the patient's head, so that the strap 26 surrounds the back of the patient's head, thereby securing the device 10 to the patient's head.

Preferably, the strap 26 is also designed to be made of a relatively elastic material to further aid in the securing process.

One of a variety of fastening systems, such as buttons, zippers or snaps can be used. However, the preferred fastening system is a hook-and-eye type fastening system such as Velcro. To that end, a longitudinal extending strip of the "eye" mating material 68 of a hook-and-eye (Velcro) type fastener is disposed upon the upper surface 71 of the strap 26 adjacent to the first end 66 thereof, and a longitudinal extending strip of the "hook" mating material 69 of a hookand-eye (Velcro) type fastener is disposed upon the lower surface 73 of the strap 26 adjacent to the second end 70 thereof. The strip of "eye" mating material 68 is sized, shaped and positioned on the upper surface 71 of the first end 66 of the strap 26, and the strip of "hook" mating material 69 is sized, shaped and positioned on the lower surface 73 of the second end 70 of the strap 26, such that the first end 66 of the strap 26 can be fastened to the second end 70 of the strap 26 by placing the "eye" fastener material 68 directly against the "hook" fastener material 69, to cause the hooks of the hook material 69 to engage the eyes of the eye material 68.

FIGS. 8 and 9, which show the device 10 upon the face of a patient.

It will be noted that ends 66, 70 of the strap 26 extend around the back of the patient's head to secure the device 10 to the patient. The device 10 is positioned on the patient so that the upper edge 62 of the eye piece 22 is disposed adjacent to the patient's eyebrows, and the lower lobes 58, 60 of the eye piece 22 rest on the patient's cheekbones. Through this sizing and shape of the eye piece shield 22, the risk is reduced substantially that a piece of flying debris will be able to strike the patient's eyes. Additionally, it will be noted that mask 12 only covers the patient's nose, leaving the patient's mouth unobstructed, to permit a dentist to insert a dental instrument as is shown in FIGS. 8 and 9. Additionally, the elbow 16 is configured on the face mask 12 so as to direct the major axial length of the gas tube 18 in a direction away from the patient's mouth, so that the tube 18 does not further obstruct the dentist from performing procedures within the patient's mouth cavity.

It should further be noted that the primary components of the device, such as the crown 32 of the mask 12, the elbow tube 16, and the eye shield 22 are preferably transparent. This transparency helps to enhance the ability of the dentist to monitor the patient's condition by causing less visual obstructions than would be caused by non-transparent components. For example, the clarity of the crown 32 enables the dentist to monitor the patient's nasal breathing, and detect any condensation build up on the crown 32. This also helps alleviate the patient's feeling of claustrophobia when the mask is affixed to the patient.

B. First Alternate and Preferred Embodiment

FIG. 1B shows an alternative embodiment of a dental anesthesia mask having an integrated eye protector 110 which includes an anesthesia mask 112, an exhaust gas line 118, an inspiratory gas line 120, and a protective eye shield 122. The inspiratory gas line 120 provides inspiratory gases to the patient while wearing the anesthesia mask 112, and the exhaust gas line 118 scavenges exhalation and other gases from the anesthesia mask 112 and surrounding vicinity. The eye mask 122 is coupled to the dental anesthesia mask having an integrated eye protector device 110 to provide eye protection for the patient as described in the previous embodiment. In the dental anesthesia mask having an integrated eye protector device 110, the inspiratory gases are delivered to the patient through the inspiratory gas line 120 and the anesthesia mask 112 functions as a hood for exhaust of gases The anesthesia face mask 112, shown separately in FIG. 2B, includes a tear-drop shaped, domed frusto-conical crown member 132 having a lower edge to which is attached a cushioning member 134. The cushioning member 134 is preferably made of a soft material and/or is inflatable to provide comfort for the patient. The cushioning member 134 also helps keep the inspiratory gases primarily within the anesthesia mask 112 though a complete seal with the patient is not necessary.

The domed frusto-conical crown member 132 of the anesthesia mask 112 includes an exhaust gas port 136, a first inspiratory gas port 121, a second inspiratory gas port 122, and a vent 142. The exhaust gas port 136 is a generally cylindrical air tube fitting port that is designed and sized to accept standard fittings of the type normally used for connection with an anesthesia mask. The exhaust gas line 118 can be coupled directly to the exhaust gas port 136, or preferably an intermediate fitting is used, such as the elbow tube 16 (See FIG. 11). The patient end 40 of the elbow tube 16 is connected to the exhaust gas port 136 of the anesthesia mask 112; and the machine end 42 of the elbow tube 16 is connected to the exhaust gas line 118. The exhaust gas line 118 is coupled at one end to the elbow tube 16 and, during use, is coupled at its other end to an exhaust gas scavenging system. The vent 142 provides a passage through which air can pass between the interior and the exterior of the anesthesia mask 112 when the device 110 is placed over the nose of the patient.

Figure 4:
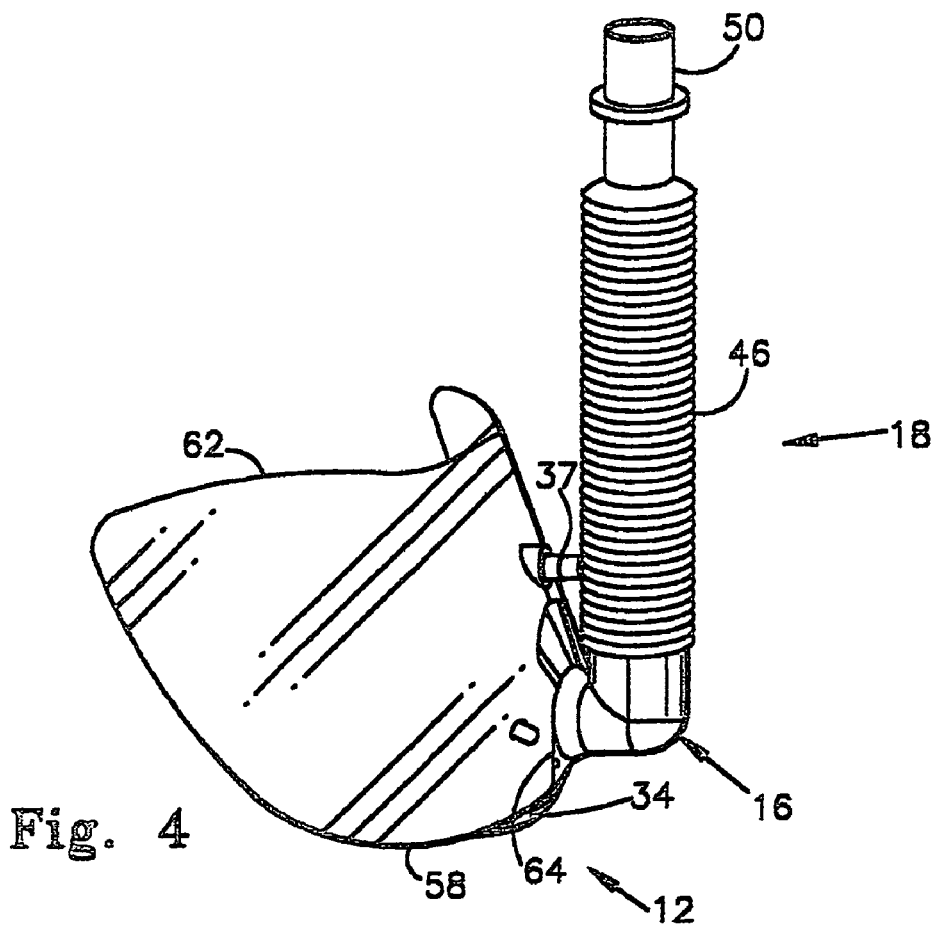
FIG. 4 is another right-side view of the present invention.
Figure 4B:
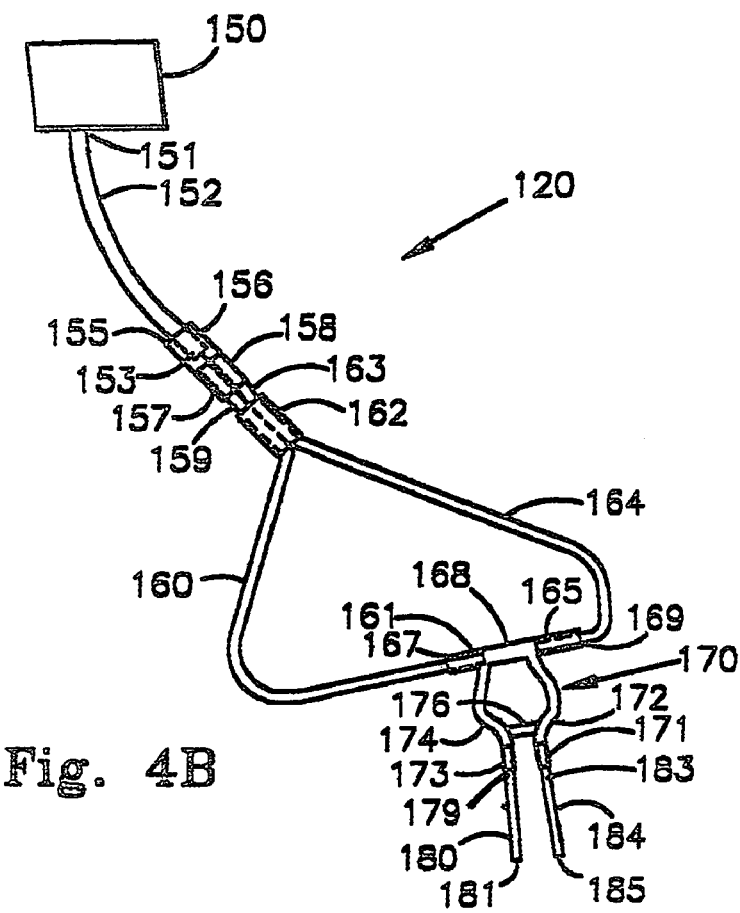
FIG. 4B is a plan view of the inspiratory line of the first alternate embodiment mask.
Figures 5, 6:
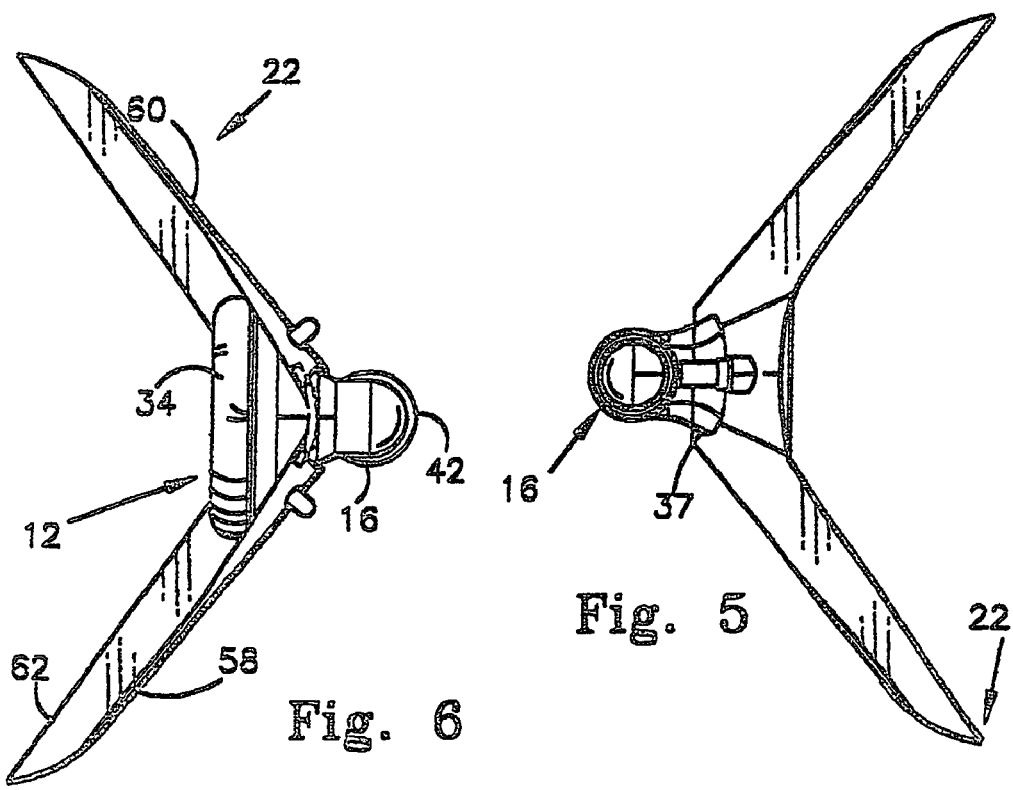
FIG. 5 is a top view of the present invention, showing the cushion member of the gface mask removed.
FIG. 6 is a bottom view of the present invention.

The first and second inspiratory gas ports 121, 122 are generally circular openings in the crown member 132 that are sized for snugly, but slideably receiving the inspiratory gas line 120 so that the inspiratory gas line can extend there through to deliver inspiratory gases directly to the patient's nose within the anesthesia face mask 112. FIG. 4B shows an inspiratory gas line 120 which includes a source line 152; a line splitter 156; first and second intermediate lines 160, 164; a slide member 162, a mask connector 170 and first and second nasal cannula 180, 184. The source line 152 is a generally cylindrical gas line used in anesthesia devices that includes a source end 151 and a patient end 153. The source end 151 is connected to an inspiration gas source 150, and the patient end 153 is connected to the line splitter 156.

The line splitter 156 includes a source end 155, a first patient end 157 and a second patient end 158. The patient end 153 of the source line 152 is connected to the source end 155 of the line splitter 156. The line splitter 156 splits the inspiratory gas flow entering through the source line 152 into two flows exiting through the first and second intermediate lines 160, 164. The first intermediate line 160 is a generally cylindrical gas line used in anesthesia devices that includes a source end 159 and a patient end 161. Similarly, the second intermediate line 164 is a generally cylindrical gas line used in anesthesia devices that includes a source end 163 and a patient end 165. The source end 159 of the first intermediate line 160 is connected to the first patient end 157 of the line splitter 156, and the patient end 161 of the first intermediate line 160 is connected to the mask connector 170. The source end 163 of the second intermediate line 164 is connected to the second patient end 158 of the line splitter 156, and the patient end 165 of the second intermediate line 164 is connected to the mask connector 170. The slide member 162 is a generally-cylindrical tubular member that fits tightly around the first and second intermediate lines 160, 164 such that it does not interfere with gas flow through the intermediate tubes 160, 164 and that it can be slidingly moved along the intermediate lines 160, 164 to a desired position and will not freely slide from that desired position. In this way the inspiratory gas line 120 can be used to secure the device 110 to the patient in place of a separate strap.

The mask connector 170 includes a source connector 168, a first and a second patient connector 172, 174 and a connecting member 176. The source connector 168 has a first entry end 167 and a second entry end 169. The first patient connector 172 has a patient end 171 and the second patient connector 174 has a patient end 173. The first and second patient connectors 172, 174 are connected to the source connector 168 such that gases entering the first and second entry ends 167, 169 of the source connector 168 can flow through the source connector into the first and second patient connectors 172, 174 and exit through the patient ends 171, 173 of the first and second patient connectors 172, 174. The connecting member 176 connects the first patient connector 172 and the second patient connector 174. The patient end 161 of the first intermediate line 160 is connected to the first entry end 167 of the source connector 168 of the mask connector 170. The patient end 165 of the second intermediate line 164 is connected to the second entry end 169 of the source connector 168 of the mask connector 170. The inspiratory gas coming from the first and second intermediate lines 160, 164 enters the entry ends 167, 169 of the mask connector 170 and exits through the patient ends 171, 173 of the patient connectors 172, 174.

The first and second nasal cannulas 180, 184 are generally flexible pieces of respiratory tubing used with anesthesia devices. The first nasal cannula 180 has a source end 179, a patient end 181, and a middle portion 193 disposed between the source end 179 and the patient end 181. The second nasal cannula 184 has a source end 183, a patient end 185, and a middle portion 195 disposed between the source end 183 and the patient end 185. The source end 179 of the first nasal cannula 180 is connected to the patient end 171 of the first patient connector 172 of the mask connector 170. The source end 183 of the second nasal cannula 184 is connected to the patient end 173 of the second patient connector 174 of the mask connector 170. The inspiratory gas coming from the first patient connector 172 of the mask connector 170 enters the source end 179 of the first nasal cannula 180 and exits through the patient end 181. The inspiratory gas coming from the second patient connector 174 of the mask connector 170 enters the source end 183 of the second nasal cannula 184 and exits through the patient end 185.

The first and second nasal cannula 180, 184 extend through the first and second inspiratory gas ports 121, 122 of the anesthesia mask 112 such that the patient ends 181, 185 of the nasal cannulas 180, 184 are under the crown member 132. The first and second inspiratory gas ports 121, 122 can be sized to form a snug fit with the first and second nasal cannula 180, 184 such that the user can move the cannula 180, 184 to place the patient ends 181, 185 in a desired position within the crown member 132 for delivery of inspiratory gas to the patient.

Figure 5B:
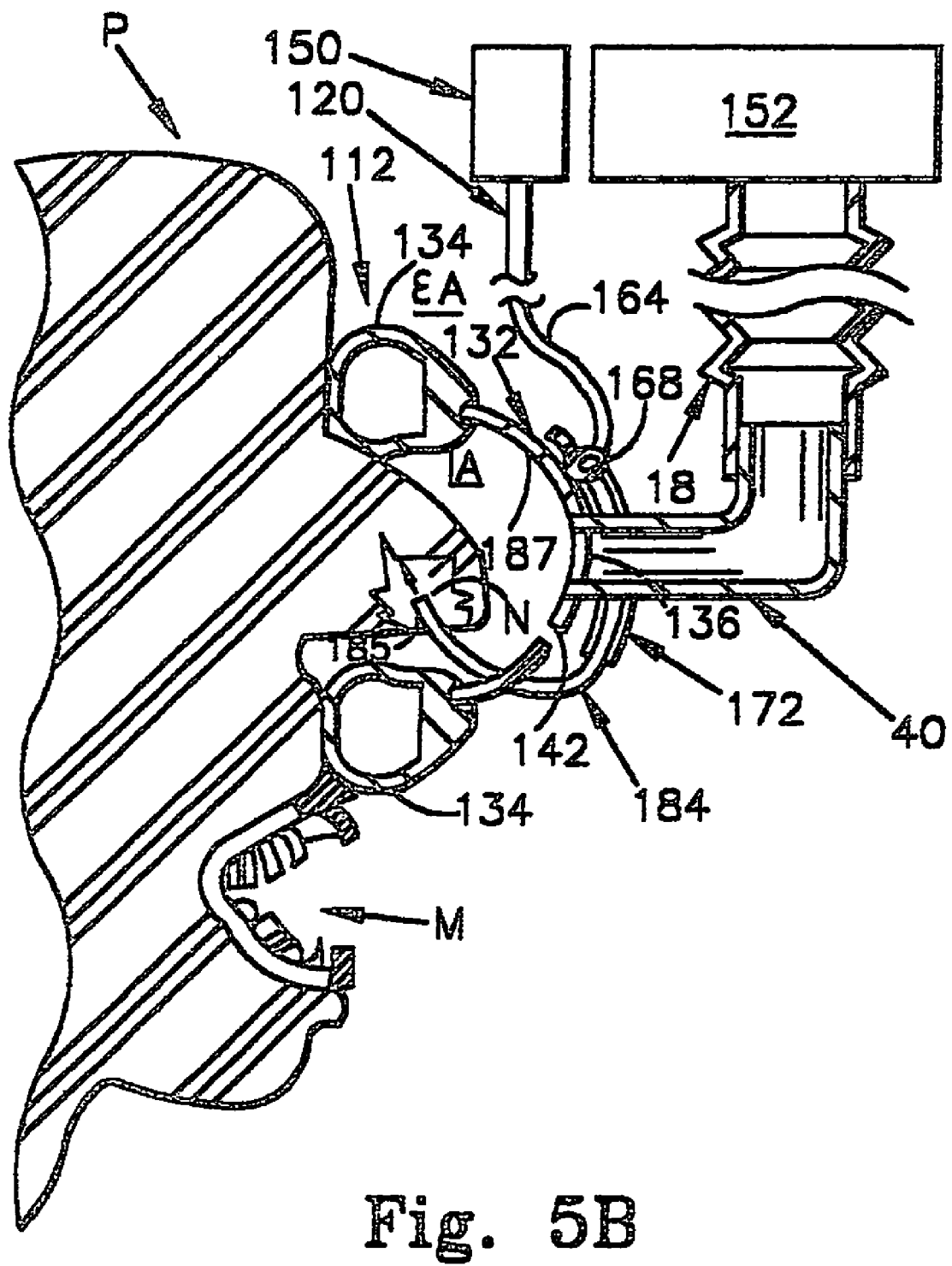
FIG. 5B is an enlarged sectional view, partly broken away taken generally along lines 5B-5B of FIG. 7B.
Figure 6B:
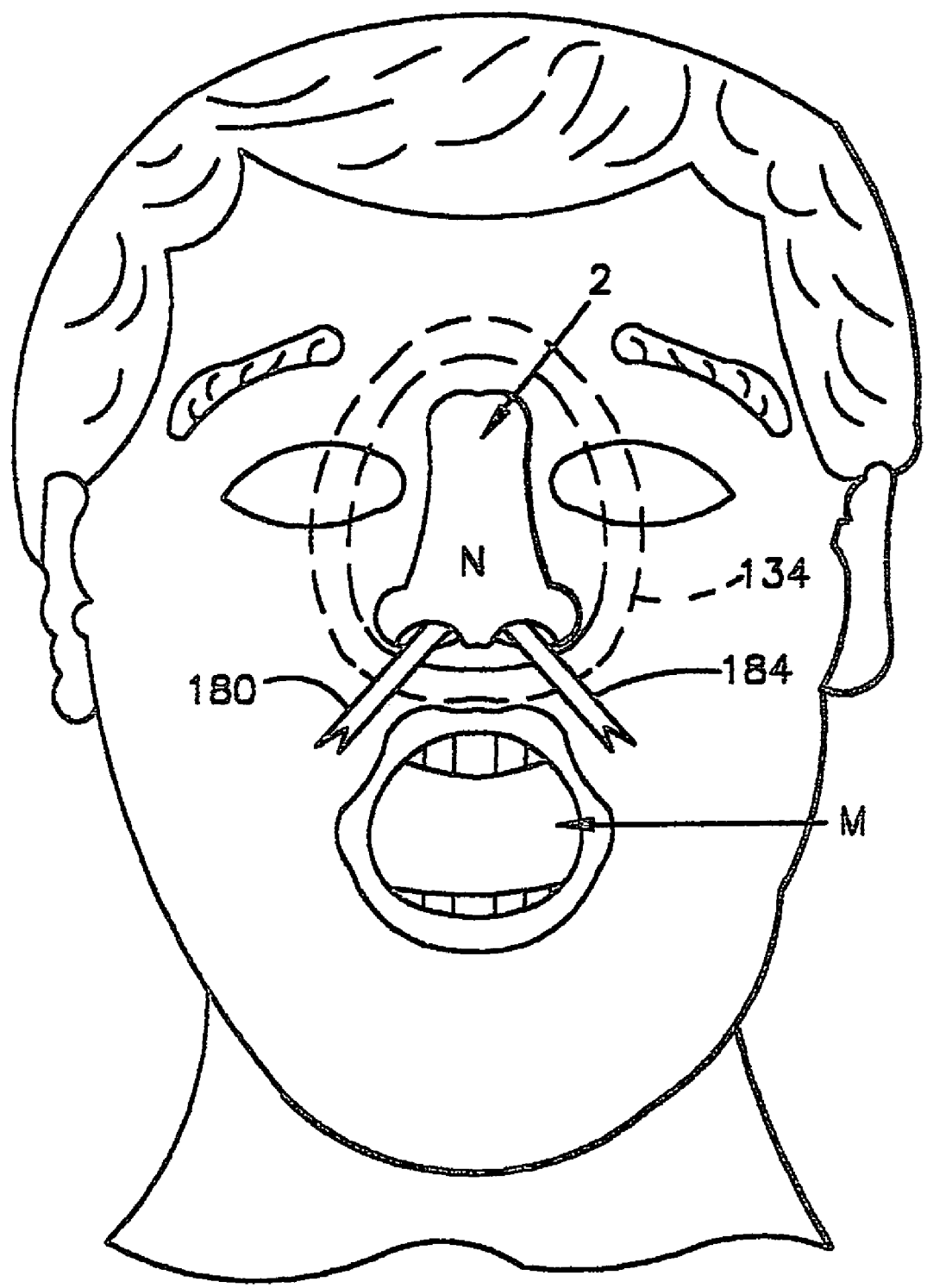
FIG. 6B is a front view of a patient illustrating the placement of the distal end of the inspiratory gas line within the nares, the mask being shown in phantom.

As best shown in FIGS. 5B and 6B, the patient ends 181, 185 of the nasal cannulas 180, 184 extend through the gas inspiratory ports 121, 122 of the crown portion 132. As the patient end 181 185 of the nasal canulas 180, 184 within the nares N of the nose Z of the patient P, the anesthesia gas is deposited directly into the nares N for inhalation by the patient. This deposition of the gas within the nares N helps to confine the gas within the nares and respiratory system of the patient P. By so doing this, it is more difficult for the gas to escape the inside area IA defined by the skin and nares of the patient and the interior surface 187 of the face mask. The inhalation performed by the patient helps to draw the anesthesia gas into the patient's P respiratory system. Also, depositing the gas within the nares N helps to prevent the gas from being sucked out of the mask by the exhaust system 152.

The inspiratory gas line 120 delivers inspiratory gases from the inspiratory gas source 150 to the patient as follows. The inspiratory gas flows from the inspiratory gas source 150 through the source line 152; through the splitter 156, which splits the flow into the first and second intermediate lines 160, 164; through the first and second intermediate lines 160, 164; through the source connector 168 and the first and second patient connectors 172, 174 of the mask connector 170; and through the nasal cannulas 180, 184 to exit from the patient ends 181, 185 of the nasal cannulas 180, 184. As the patient ends 181, 185 of the nasal canulas 180, 184 are positioned within the nares N (FIG. 5B), the anesthesia gas is deposited directly into the nasal cavity of the patient. Notice also that the mouth M (FIGS. 5B, 6B) is uncovered, thereby permitting clear access to the mouth of the patient P by the dentist or oral surgeon. The components of the inspiratory gas line 120 fit together such that the inspiratory gas stays within the inspiratory gas line 120 between the source end 151 of the source line 152 and the patient ends 181, 185 of the nasal cannulas 180, 184. The components of the inspiratory gas line 120 are also preferably clear.

Figure 2B:
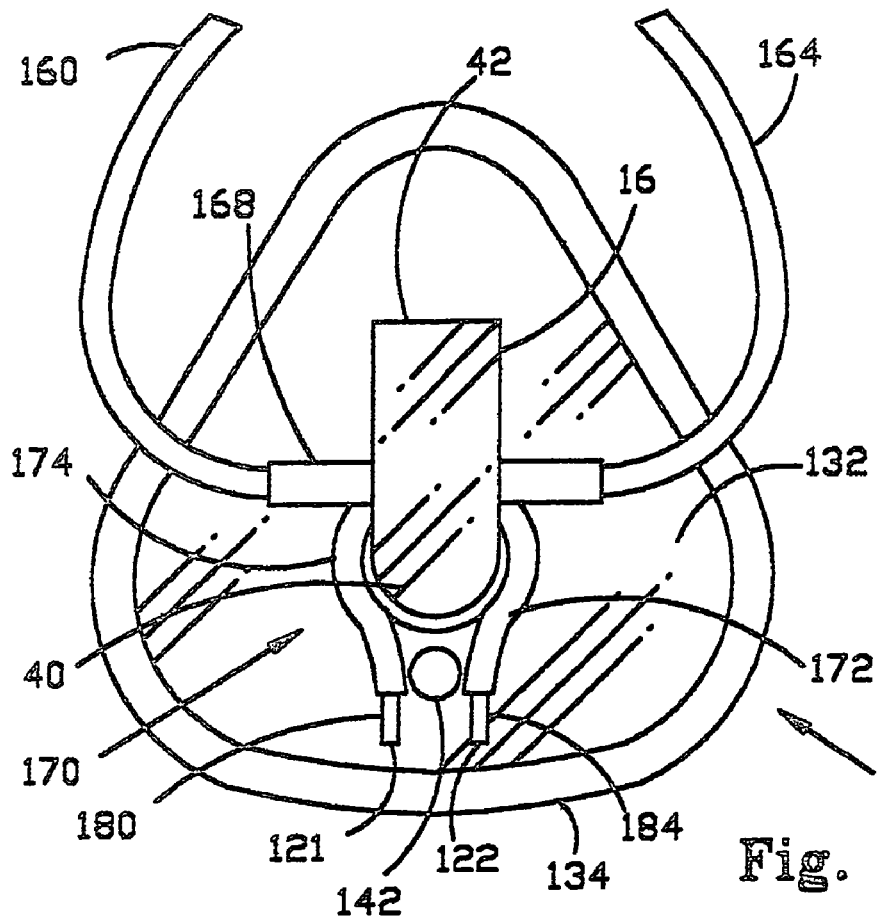
FIG. 2B is a front view of the first alternate embodiment showing the shield removed.
Figure 3:
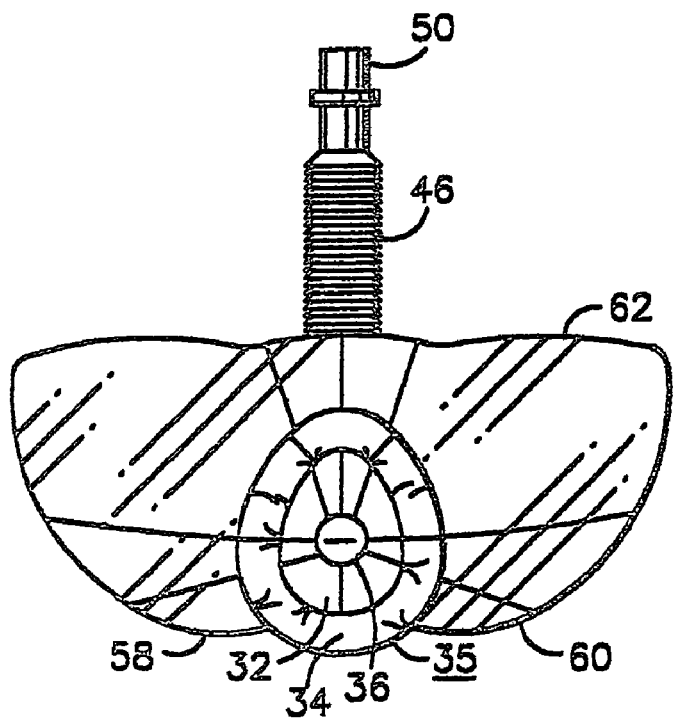
FIG. 3 is a rear view of the present invention.
Figure 3B:
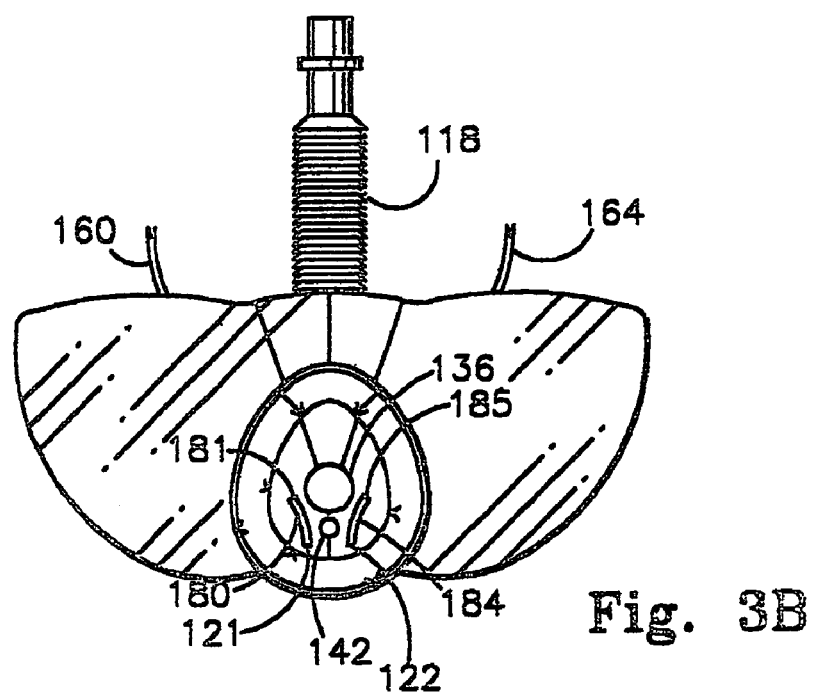
FIG. 3B is a rear view of the first alternate embodiment mask.

The mask connector 170 secures the inspiratory gas line 120 to the anesthesia mask 112. Referring to FIG. 4B, it can be seen that the source connector 168, the first and second patient connectors 172, 174, and the connecting member 176 of the mask connector 170 form an encircled opening. As shown in FIG. 2B, this encircled opening can be fit over the exhaust port 136 and the elbow tube 16 connected to the anesthesia mask 112 to connect the inspiratory gas line 120 to the anesthesia mask 112. The mask connector 170 is preferably sized such that the mask connector 170 fits firmly over the elbow tube 16.

Figure 7:
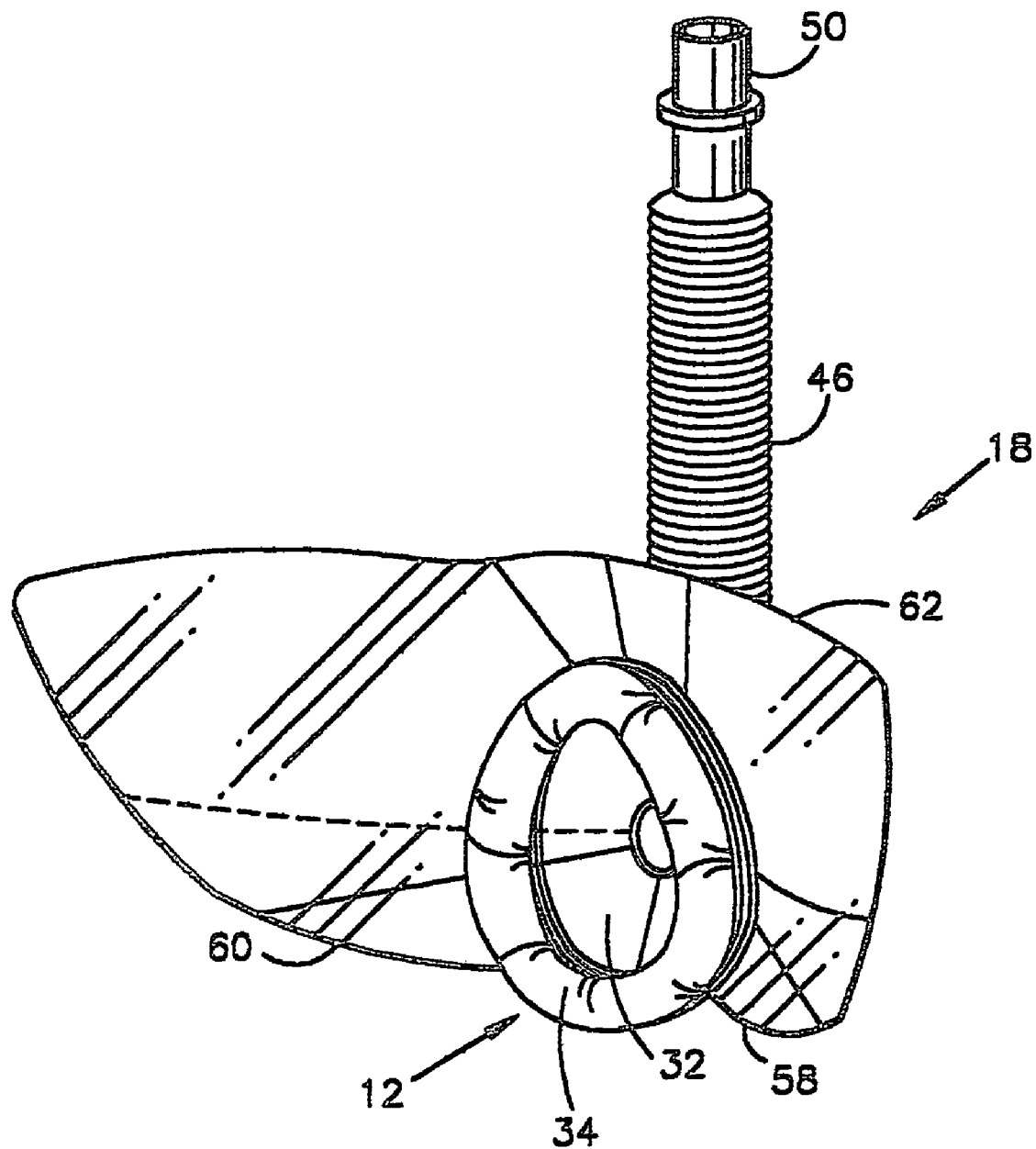
FIG. 7 is a rear, perspective view of the present invention.
Figure 7B:
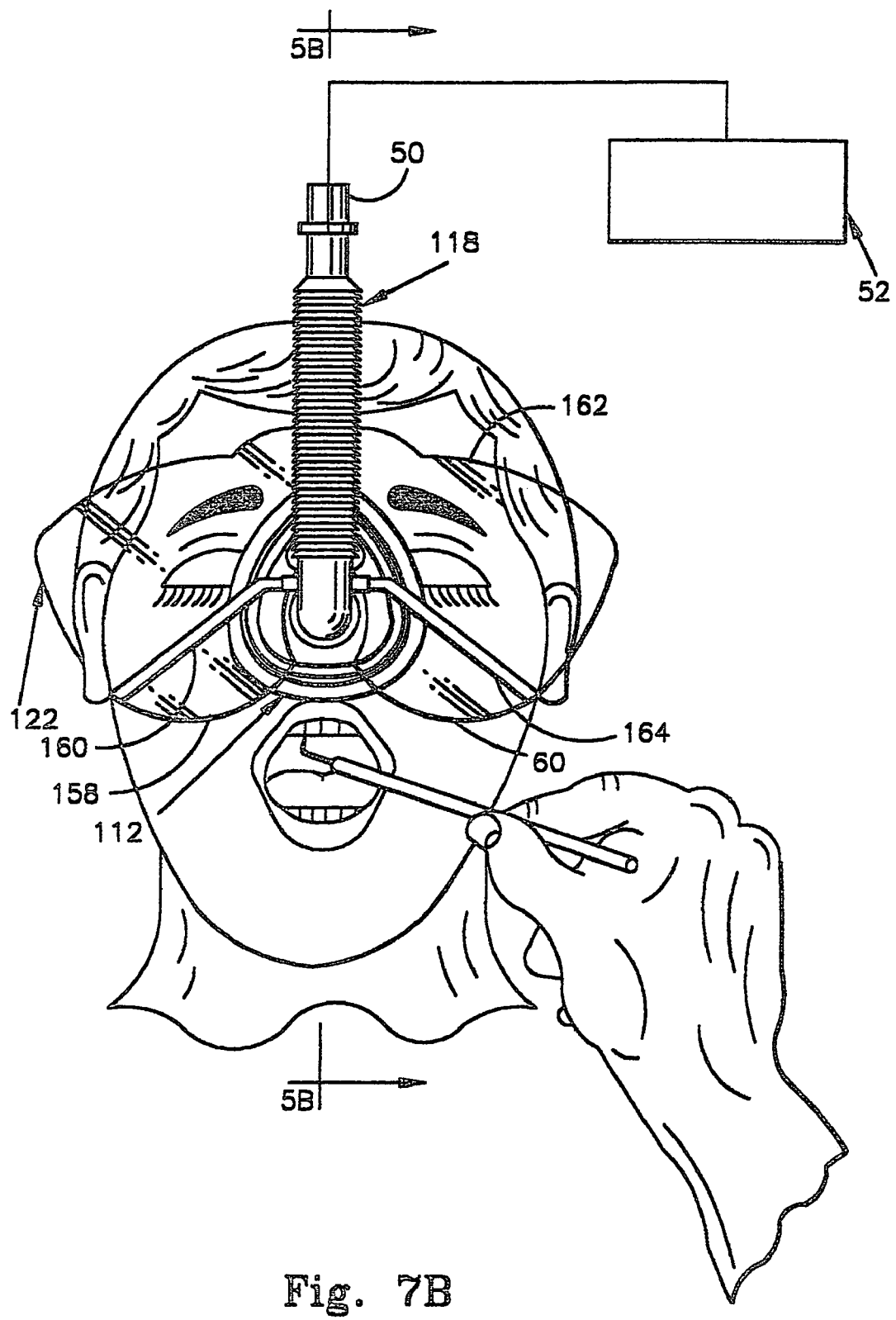
FIG. 7B is a front view of the first alternate embodiment mask as placed on a patient.

The connection between the first and second intermediate lines 160, 164 of the inspiratory gas line 120 and the anesthesia mask 112 also allows the inspiratory gas line 120 to secure the device 110 to the patient and to hold the eye shield 22 against the face of the patient as shown in FIG. 7B. The device 110 is attached to the patient by placing the anesthesia mask 112 over the nose of the patient and the intermediate lines 160, 164 over the eye shield 22 and on opposite sides of the patient's head. The slide member 162 of the inspiratory gas line 120 is then slid along the first and second intermediate lines 160, 164 such that the inspiratory gas line 120 holds the anesthesia mask 112 against the face of the patient surrounding the nose area, and holds the eye shield 22 against the face of the patient protecting the eyes.

When using the device 110 to administer anesthesia to a patient, the flow rate of inspiratory gas through the inspiratory gas line 120 is usually less then the flow of gas being scavenged through the exhaust line 118. For example, when administering nitrous oxide, the inspiratory gas flow rate is normally about 10 liters/minute of a mixture containing approximately 60% oxygen and 40% nitrous; while the exhaust gas flow rate is approximately 45 liters/minute. The patient ends 181, 185 of the nasal cannula 180, 184 are preferably inserted into the nares of the patient, creating a double chamber within the anesthesia mask 112. The inspiratory gas is delivered directly into the nares of the patient creating an inner chamber within the patient's nose, and the exhaust gas is being scavenged by the exhaust gas line from within the anesthesia mask 112 and outside the patient's nose. The additional gas needed to satisfy the greater exhaust flow rate is pulled into the mask through the vent 142 and from under the cushion member 134 of the anesthesia mask 112. The inner chamber, formed within patient's nares, is fed by the patient ends 181, 185 of the nasal cannulas 180, 184; and the outer chamber, formed outside patient's nose and within anesthesia mask 112, is fed by nasal exhalation of patient and the vent 142 in the anesthesia mask 112.

It is preferable that the inspiratory gas ports 121, 122 form a snug, friction fit with the nasal cannula 180, 184 to permit the provider to adjust the depth of the length of the nasal cannula 180, 184 within the anesthesia mask 112 to position the patient ends 181, 185 within the nares of the patient's nose. It is also preferable that the vent 142 is located on the lower end of the anesthesia mask 112 so that it will be near the mouth during use. This increases the amount of expiratory gases exhaled through the patient's mouth that are scavenged through the vent 142 further reducing the release of unwanted inspiratory gases exhaled by the patient into the environment.

In alternative embodiments a one-way flow valve can be used in place of the vent 142. The one-way flow valve, as described in the following three embodiments: allows air to flow into the anesthesia mask to compensate for greater exhaust flow rate, but does not allow gases to exit from the anesthesia mask which would allow inspiratory gases into the user environment EA, exteriorly adjacent to the face mask 112.

FIG. 8B shows a one-way flow mask valve 204 in an anesthesia mask 212. The other aspects of the anesthesia mask 212, the inspiratory gas line 120, and the exhaust gas line 118 are as described in the previous alternate embodiment shown in FIGS. 1B-7B. The one-way mask flow valve 204 allows gas from outside the anesthesia mask 212 to flow into the anesthesia mask 212 but does not allow gas from the inner environment IA within the anesthesia mask 212 to the outside environment EA through the mask valve 204. This would help prevent gases from within the anesthesia mask 112 to escape into the outside environment when the patient rapidly exhales through their nose, while still allowing the outside gases to flow into the anesthesia mask 112 through the mask valve 204 to satisfy the greater exhaust flow rate through the exhaust line 118 than the inspiratory flow rate through the inspiratory line 120.

FIG. 9B shows a T-shaped connector 316 used in place of the elbow tube 16. The T-connector includes a first leg connector 330, a second leg connector 332, and a third leg connector 334 such that gases can flow freely between any of the first, second and third leg connectors 330, 332, 334. The first, second and third leg connectors 330, 332, 334 are generally cylindrical air tube fitting ports that are designed and sized to accept standard fittings of the type normally used for connection with an anesthesia mask. The anesthesia face mask 312 includes a tear-drop shaped frusto-conical crown member 332 having a lower edge to which is attached a cushioning member 134. The frusto-conical crown member 332 includes an exhaust gas port 336, a first inspiratory gas port 321 and a second inspiratory gas port 322. The exhaust gas port 336 and the first and second inspiratory gas ports 321, 322 perform the same functions as described in the previous embodiment for the exhaust gas port 136 and the first and second inspiratory gas ports 121, 122, respectively. The first leg 330 of the T-connector 316 is connected to the exhaust gas port 336 of the anesthesia mask 312; the second leg 332 of the T-connector 316 is connected to the exhaust gas line 118, and the third leg 334 of the T-connector 316 is connected to a one-way flow valve 340. The inspiratory gas line 120, and the exhaust gas line 118 are as described in the previous embodiment.

The one-way flow valve 340 allows gas from the exterior area EA outside the anesthesia mask 312 and T-connector 316 to flow into the T-connector 316 but does not allow gas from within the anesthesia mask 312 and the T-connector 316 flow into the outside environment through the one-way flow valve 340. This helps prevent gases from within the anesthesia mask 312 to escape into the outside environment when the patient rapidly exhales through their nose, while still allowing the outside gases to flow into the T-connector 316 through the one-way valve 340 to satisfy the greater exhaust flow rate through the exhaust line 118 than the inspiratory flow rate through the inspiratory line 120.

FIG. 10B schematically illustrates a Y-shaped connector 416 used in place of the T-connector 316. The Y-connector includes a first leg connector 430, a second leg connector 432, and a third leg connector 434 such that gases can flow freely between any of the first, second and third leg connectors 430, 432, 434. The first, second and third leg connectors 430, 432, 434 are generally cylindrical air tube fitting ports that are designed and sized to accept standard fittings of the type normally used for connection with an anesthesia mask. The anesthesia face mask 312, the inspiratory gas line 120, and the exhaust gas line 118 are as described in the previous embodiment.

The first leg 430 of the Y-connector 416 is connected to the exhaust gas port 336 of the anesthesia mask 312; the second leg 432 of the Y-connector 416 is connected to the exhaust gas line 118, and the third leg 434 of the Y-connector 416 is connected to a one-way flow valve 440. The one-way flow valve 440 allows gas from outside the anesthesia mask 312 and Y-connector 416 to flow into the Y-connector 416 but does not allow gas from within the anesthesia mask 312 and the Y-connector 416 to flow into the outside environment through the one-way flow valve 440. This helps prevent gases from within the anesthesia mask 312 to escape into the outside environment when the patient rapidly exhales through their nose, while still allowing the outside gases to flow into the Y-connector 416 through the one-way valve 440 to satisfy the greater exhaust flow rate through the exhaust line 118 than the inspiratory flow rate through the inspiratory line 120.

Applicant conducted some preliminary experiments to measure the efficacy of the present invention. The experiments were conducted on three separate days in two dental surgical rooms on each day. Nitrous oxide concentrations were measured in each room on each day using VAPOR-TRAK Nitrous Oxide Monitors distributed by Kem Medical Products, Fort Lauderdale, Fla. which were sealed after use and sent to Kem Medical Products for determination of results. Three nitrous oxide monitors were used in each room; two placed on the headrest of the patient chair near the patient's head, and a third monitor was worn by the doctor. On each occasion, a total of 10 liters/minute of inspiratory gas was administered, 6 liters being oxygen and 4 liters being nitrous. Patients were then treated in the normal fashion at which time an IV anesthetic was administered if desired by the patient. The IV was started in the right antecubital fossa, and after an appropriate time with 25 mg of Demerol and 5 mg of Versed, local anesthetic was injected into the appropriate areas for removal of wisdom teeth. The patient would then be given time for the local anesthetic to work during which time they may have talked to the assistant. After about 10-15 minutes for the onset of the local anesthetic, the surgery would be done for the removal of four wisdom teeth on the maxillary and mandibular right and left sides. Each case took between 30 and 45 minutes, most cases running 45 minutes in length. After completion of the last third molar, the nitrous oxide was discontinued and the patient was given 100% oxygen via the anesthesia delivery system. When viewing the following experimental results, the reader is reminded that the ADA guidelines recommend a N2O concentration of less than or equal to 50 ppm.

On the first day, five patients were treated in Room A and four patients were treated in room B using the prior art Porter anesthesia mask delivery system The time weighted concentrations of the two headrest monitors in Room A were 120.4 and 135 ppm N2O; respectively; and in Room B were 121 and 140 ppm N2O, respectively. The eight hour time weighted concentration measured by the doctor's monitor was 146 ppm N2O. During this day the N2O was never started until the mask was placed over the patient's nose, however the mask would lift off the patient's nasal area during application of the local anesthetic and many times during removal of the upper wisdom teeth. On this day, the readings in both rooms were significantly above the ADA guidelines.

On the second day, an identical number of patients were treated in Rooms A and B as on the first day using the second embodiment of the present invention The time weighted concentrations of the two headrest monitors in Room A were 49.15 and 43.05 ppm N2O. Unfortunately, the Room B measurements were compromised due to procedural problems. The doctor's monitor reading was also compromised because the doctor treated another patient using the Porter anesthesia mask delivery system, thus exposing the doctor to N2O released during the procedure using the Porter mask. The experiment was repeated on a third day using the second embodiment of the present invention to verify the uncompromised results from the second day. Additionally, on the third day a baseline measurement was taken in Room A which measured a N2O concentration of 2.0 ppm. The time weighted concentrations measured by one of the headrest monitors in Room A over 1.5 hours during which two procedures were performed was 12.92 ppm N2O. The results from the second monitor were not available at the time of filing. The time weighted concentrations measured in Room B were 25.14 and 26.89 ppm N2O, respectively. The results from the doctor's monitor were not available at the time of filing. These results from the second and third day show that the N2O concentrations using the present invention in an uncompromised environment are a significant improvement over present anesthesia delivery devices, and are significantly below the ADA guidelines.

The Applicant believes the test results show that the present invention is a significant improvement in administering and scavenging nitrous oxide. Also, patients commented that the present invention was lighter and more comfortable than the Porter mask. One patient also said it was much easier to move their head for the surgical procedure, and she did not feel as closed-in or claustrophobic with the present invention as she felt with the Porter mask.

Having described the invention in detail, it will be appreciated that variations and modifications can exist within the scope and spirit of the invention as defined by the appended claims.

What is claimed is:

1. An anesthesia delivery device capable of being coupled to a ventilation system comprising an inspiratory gas input for delivering gas to a patient and an exhaust gas output for delivering gas from the patient to the ventilation system, the anesthesia delivery device comprising:
   an inspiratory gas line having a machine end and a patient end portion, the machine end being capable of being fluidly coupled to the inspiratory gas input of the ventilation system, and the patient end portion being configured for being received within the naris of the patient for delivering inspiratory gas to the naris of the patient,
   a face mask comprising a dome portion sized to cover the patient's nose without covering the patient's mouth, the dome portion defining an inside air space between the patient's nose and the dome portion, and an outside air space exterior of the dome portion, the dome portion including a gas port, the patient end portion comprising a flexible cannula having a source end disposed in the outside air space, a middle portion extending through the dome portion, and a patient end configured for being received within the naris of the patient for delivering inspiratory gas to the naris of the patient, the gas port of the face mask being sized to slidably receive the flexible cannula for permitting the user to move the cannula relative to the face mask and gas port to enable a user to place an end of the flexible cannula in a desired position within the naris of the patient
   a vent for allowing gas to pass between the inside air space and the outside air space, and an exhaust port capable of being fluidly coupled to the exhaust gas output of the ventilation system for allowing gas to pass from the inside air space to the exhaust gas output of the ventilation system;
   wherein the exhaust port and vent are capable of cooperatively exerting a negative pressure on the outside air space adjacent to the face mask for preventing inspiratory gases from entering the outside air space adjacent to the face mask.

2. The anesthesia delivery device of claim 1 further comprising an eye shield having a shield attachment mechanism for attaching the eye shield to the face mask such that the eye shield covers the eyes of the patient.

3. The anesthesia delivery device of claim 1 wherein the vent is formed as a part of the face mask.

4. The anesthesia delivery device of claim 3 wherein the dome portion includes a lower edge, further comprising a cushion member attached to the lower edge of the dome portion of the face mask, wherein the cushion member contains a bladder filled with a gas, and is scented.

5. The anesthesia delivery device of claim 1 wherein the inspiratory gas line comprises a mask connector member for connecting the inspiratory gas line to the face mask.

6. The anesthesia delivery device of claim 5 wherein the inspiratory gas line further comprises a first side line, a second side line, and a slide member; wherein inspiratory gases pass between the machine end and the patient end of the inspiratory gas line through both the first side line and the second side line; wherein the slide member surrounds the first and second side lines and is slideable along the first and second side lines allowing the first and second side lines to be placed on opposite sides of the patient's head and the slide member can be positioned to create a snug fit of the inspiratory gas line around the head of the patient to hold the anesthesia delivery device in place.

7. The anesthesia delivery device of claim 1 further comprising an exhaust connector connected to the exhaust port of the face mask and capable of being fluidly coupled to the exhaust gas output of the ventilation system for allowing gas to pass from the inside air space to the exhaust gas output of the ventilation system, the exhaust connector including the vent, wherein the vent comprises a one way valve for permitting air to flow into the exhaust connector from the outside air space, while preventing air from flowing to the outside air space from the exhaust connector.

8. The anesthesia delivery device of claim 7 further comprising a strap for attaching the anesthesia delivery device to the patient's head, wherein the face mask further comprises a left post extending into the outside air space on one side of the exhaust port and a right post extending into the outside air space on the opposite side of the exhaust port; and wherein the strap further comprise a first attachment point and a second attachment point; the first attachment point being capable of attachment to the right post of the face mask and the second attachment point being capable of attachment to the left post of the face mask.

9. The anesthesia delivery device of claim 7 further comprising an exhaust line attached to the exhaust port of the face mask, and a strap for attaching the anesthesia delivery device to the patient's head, wherein the strap further comprises an attachment mechanism for attaching to the exhaust line to secure the anesthesia delivery device to the patient's head.

10. The anesthesia delivery device of claim 9 wherein the attachment mechanism of the strap is a slit in the strap, wherein the slit is capable of being placed around the exhaust line.

11. The anesthesia delivery device of claim 7 further comprising a strap for attaching the anesthesia delivery device to the patient's head, wherein the strap further comprises a right side having a proximal end and a distal end, the proximal end of the right side of the strap being attached to the face mask on the right side of the patient's head and the distal end of the right side having a first fastening piece; and a left side having a proximal end and a distal end, the left side of the patient's head and the distal end of the left side having a second fastening piece; the first fastening piece being capable of being mainly connected to the second fastening piece.

12. The anesthesia delivery device of claim 11 wherein the first fastening piece comprises the hook material of a Velcro fastener, and the second fastening piece comprises the eye material of a Velcro fastener.

13. The anesthesia delivery device of claim 1 wherein the vent comprises an aperture in the face mask.

14. The anesthesia delivery device of claim 1 wherein the vent is a one-way flow valve allowing the flow of gas into the inside air space of the dome portion of the mask through the vent, but not allowing the flow of gas out of the inside air space of the dome portion of the mask through the vent.

15. The anesthesia delivery device of claim 1 wherein the patient end portion includes a second flexible cannula having a source end disposed in the outside air space, a middle portion extending through the dome portion, and a patient end configured for being received within the naris of the patient for delivering inspiratory gas to the naris of the patient.

16. The anesthesia delivery device of claim 15 wherein each of the first and second cannulas comprise flexible respiratory tubing.

17. The anesthesia delivery device of claim 1 wherein the first inspiratory port is sized for slidably but snugly receiving the first cannula therein to permit the user to vary the length of the first cannula within the inside air space and for snugly engaging the first cannula to resist movement of the first cannula when not being moved by the user.

18. The anesthesia delivery device of claim 17 wherein the patient end portion includes a second flexible cannula having a source end, and a patient end, wherein the dome portion includes a second inspiratory port through which the middle portion of the second cannula passes, the second inspiratory port being sized for slidably but snugly receiving the second cannula therein to permit the user to vary the length of the second cannula within the inside air space and for snugly engaging the second cannula to resist movement of the second cannula when not being moved by the user.

19. An anesthesia delivery device capable of being coupled to a ventilation system comprising an inspiratory gas input for delivering gas to the a patient and an exhaust gas output for delivering gas from the patient to the ventilation system, the anesthesia delivery device comprising:
   an inspiratory gas line having a machine end and a patient end portion, the machine end being capable of being fluidly coupled to the inspiratory gas input of the ventilation system, and the patient end portion being configured for being received within the naris of the patient for delivering inspiratory gas to the naris of the patient,
   a face mask comprising a dome portion sized to cover the patient's nose without covering the patient's mouth, the dome portion defining an inside air space between the patient's nose and the dome portion, and an outside air space exterior of the dome portion,
   a vent for allowing gas to pass between the inside air space and the outside air space,
   an exhaust port capable of being fluidly coupled to the exhaust gas output of the ventilation system for allowing gas to pass from the inside air space to the exhaust gas output of the ventilation system, the exhaust port including an elbow, and
   an exhaust line having a machine end and a patient end, the patient end being connected to the elbow of the exhaust port for scavenging gases from the inside air space of the dome portion, the exhaust line being positioned by the elbow to extend over the forehead of the patient
   wherein the exhaust port and vent are canable of cooperatively exerting a negative pressure on the outside air space adjacent to the face mask for preventing inspiratory gases from entering the outside air space adjacent to the face mask and
   wherein the patient end portion comprises a flexible cannula having a source end disposed in the outside air space, a middle portion slidably but snugly received by, and extending through an inspiratory port in the face mask, and a patient end configured for being received within the naris of the patient for delivering inspiratory gas to the naris of the patient.

20. An anesthesia delivery device capable of being coupled to a ventilation system comprising an inspiratory gas input for delivering gas to a patient and an exhaust gas output for delivering gas from the patient to the ventilation system, the anesthesia delivery device comprising:
   an inspiratory gas line having a machine end and a patient end portion, the machine end being capable of being fluidly coupled to the inspiratory gas input of the ventilation system, and the patient end portion being configured for being received within a naris of the patient for delivering inspiratory gas to the naris of the patient,
   a facemask comprising a dome portion sized to cover the patient's nose without covering the patient's mouth, the dome portion defining an inside air space between the patient's nose and the dome portion, and an outside air space exterior of the dome portion, the face mask further including an inspiratory gas port and an exhaust port;

the patient end portion comprising a flexible cannula having a source end disposed in the outside air space, a middle portion extending through the dome portion, and a patient end configured for being received within the naris of the patient for delivering inspiratory gas to the naris of the patient, the inspiratory gas port of the face mask being sized to slidably receive the flexible cannula for permitting the user to slidably move the cannula relative to the face mask to place the patient end of the flexible cannula in a desired position within the naris of the patient, a vent for allowing gas to pass between the inside air space and the outside air space, and an exhaust connector connected to the exhaust port of the face mask and capable of being fluidly coupled to the exhaust gas output of the ventilation system for allowing gas to pass from the inside air space to the exhaust gas output of the ventilation system;

wherein the exhaust port and vent are capable of cooperatively exerting a negative pressure on the outside air space adjacent to the face mask for preventing inspiratory gases from entering the outside air space adjacent to the face mask.

21. The anesthesia delivery device of claim 20 wherein the exhaust connector is bifurcated, having a first leg, a second leg and a third leg wherein gas can flow freely between the first, second and third legs; the first leg being attached to the exhaust port, the second leg capable of being fluidly coupled to the exhaust gas output of the ventilation system, the third leg coupled to the vent, the vent comprising a one-way flow valve allowing the flow of gas into the exhaust connector through the third leg but not allowing the flow of gas out of the third leg through the vent.

22. The anesthesia delivery device of claim 21 wherein the exhaust connector is T-shaped.

23. An anesthesia delivery device capable of being coupled to a ventilation system comprising an inspiratory gas input for delivering gas to a patient and an exhaust gas output for delivering gas from the patient to the ventilation system, the anesthesia device comprising:

a face mask comprising a dome portion having a lower edge, the dome portion being sized to cover the patient's nose without covering the patient's mouth, the dome portion defining an inside air space between the patient's nose and the dome portion, and an outside air space exterior of the dome portion, a cushion member attached to the lower edge of the dome portion, and an exhaust port for allowing gas to pass from the inside air space of the dome portion;

a vent for allowing gas to pass between the inside air space and the outside air space, an exhaust port for allowing gas to pass from the inside air space of the dome portion, the exhaust port including an elbow;

an inspiratory port;

an inspiratory gas line having a machine end and a patient end, the machine end being located in the outside air space and being capable of being fluidly coupled to the inspiratory gas input of the ventilation system, and the patient end being located in the inside air space and being configured for being received within the naris of the patient for delivering inspiratory gas to the naris of the patient, the inspiratory gas line passing from the outside air space into the inside air space through the inspiratory port; and an exhaust line having a machine end and a patient end, the machine end being capable of being fluidly coupled to the exhaust gas output of the ventilation system, and the patient end being connected to the elbow of the exhaust port for scavenging gases from the inside air space of the dome portion, the exhaust line being positioned by the elbow to extend over the forehead of the patient;

wherein the exhaust port and vent are capable of cooperatively exerting a negative pressure on the outside air space adjacent to the face mask for preventing inspiratory gases from entering the outside air space adjacent to the face mask.

24. The anesthesia delivery device of claim 23 wherein the inspiratory port of the face mask is sized to slidably but snugly receive the flexible cannula for permitting the user to move the cannula relative to the face mask and inspiratory gas port to enable a user to adjust the length of the cannula within the inside air space so that the cannula is properly positioned within the naris of the patient; wherein the cushion member is a bladder filled with a gas; and wherein the face mask further comprises an inflation valve for increasing or decreasing the gas pressure within the bladder.

25. The anesthesia delivery device of claim 23 wherein the inspiratory gas line further comprises a first side line, a second side line, and a slide member; wherein inspiratory gases pass between the machine end and the patient end of the inspiratory gas line through both the first side line and the second side line; wherein the slide member surrounds the first and second side lines and is slidable along the first and second side lines allowing the first and second side lines to be placed on opposite sides of the patient's head and the slide member can be positioned to create a snug fit of the inspiratory gas line around the head of the patient to hold the anesthesia delivery device in place.

26. The anesthesia delivery device of claim 23 further comprising a strap for attaching the anesthesia delivery device to the patient's head.

27. The anesthesia delivery device of claim 26 wherein the strap has a right end, a left end and a central portion being disposed between the right end and the left end; and further comprises an aperture located in the central portion, the aperture being fit around the exhaust line for attaching the strap to the anesthesia delivery device, a first fastening piece located on the right end of the strap, and a second fastening piece located on the left end of the strap, the first fastening piece being capable of being mainly connected to the second fastening piece for attaching the anesthesia delivery device to the patient's head.

28. The anesthesia delivery device of claim 23 wherein the vent is a one-way flow valve allowing the flow of gas into the inside air space of the dome portion of the mask through the vent, but not allowing the flow of gas out of the inside air space of the dome portion of the mask through the vent.

29. An anesthesia delivery device capable of being coupled to a ventilation system comprising an inspiratory gas input for delivering gas to a patient and an exhaust gas output for delivering gas from the patient to the ventilation system, the anesthesia delivery device comprising:

a face mask comprising
a dome portion having a lower edge, the dome portion being sized to cover the patient's nose without covering the patient's mouth, the dome portion defining an inside air space between the patient's nose and the dome portion, and an outside air space exterior of the dome portion, a flow vent for allowing the flow of gas into the inside air space through the vent, an exhaust port for allowing gas to pass from the inside air space of the dome portion; and an inspiratory port;

an inspiratory gas line having a machine end and a patient end portion, the machine end being located in the outside air space and being capable of being fluidly coupled to the inspiratory gas input of the ventilation system, and the patient end portion, the patient end portion comprising a flexible cannula having a source end disposed in the outside air space, a middle portion slidably but snugly received in the inspiratory port to extend through the dome portion, and a patient end configured for being received within the naris of the patient for delivering inspiratory gas to the naris of the patient, an exhaust line having a machine end and a patient end, the machine end being capable of being fluidly coupled to the exhaust gas output of the ventilation system, and the patient end being connected to the exhaust port for scavenging gases from the inside air space of the dome portion; and an eye shield having a shield attachment mechanism for attaching the eye shield to the face mask such that the eye shield covers the eyes of the patient;

wherein the exhaust port and vent are capable of cooperatively exerting a negative pressure on the outside air space adjacent to the face mask for preventing inspiratory gases from entering the outside air space adjacent to the face mask.

30. The anesthesia delivery device of claim 29 wherein the face mask includes a scenting material to impart a scent to the face mask.

31. The anesthesia delivery device of claim 30 wherein the scenting material is chosen from a group of scenting materials including fruit scented scenting materials, candy scented scenting materials, flower scented scenting materials, spice scented scenting materials, potpourri scented scenting materials, perfume scented scenting material, gum scented scenting materials, food scented scenting material, and plant scented scenting materials.

32. The anesthesia delivery device of claim 1 wherein the inspiratory gas port of the face mask is sized to slidably but snugly receive the flexible cannula to enable a user to adjust the length of the cannula within the inside air space so that the cannula is properly positioned within the naris of the patient.

33. An anesthesia delivery device capable of being coupled to a ventilation system comprising an inspiratory gas input for delivering gas to a patient and an exhaust gas output for delivering gas from the patient to the ventilation system, the anesthesia delivery device comprising:

an inspiratory gas line having a machine end and a patient end portion, the machine end being capable of being fluidly coupled to the inspiratory gas input of the ventilation system, and the patient end portion being configured for being received within the naris of the patient for delivering inspiratory gas to the naris of the patient, a face mask comprising a dome portion sized to cover the patient's nose without covering the patient's mouth, the dome portion defining an inside air space between the patient's nose and the dome portion, and an outside air space exterior of the dome portion, the patient end portion comprising a flexible cannula having a source end disposed in the outside air space, a middle portion extending through the dome portion, and having a length disposed within the dome portion, wherein the length of the middle portion disposed within the dome portion is variable by the user, and a patient end disposed within the dome portion and being configured for being received within the naris of the patient for delivering inspiratory gas to the naris of the patient, a vent for allowing gas to pass between the inside air space and the outside air space, and an exhaust port capable of being fluidly coupled to the exhaust gas output of the ventilation system for allowing gas to pass from the inside air space to the exhaust gas output of the ventilation system;

wherein the exhaust port and vent are capable of cooperatively exerting a negative pressure on the outside air space adjacent to the face mask for preventing inspiratory gases from entering the outside air space adjacent to the face mask.

* * * * *